United States Patent
Oltean et al.

(10) Patent No.: US 6,299,307 B1
(45) Date of Patent: *Oct. 9, 2001

(54) EYE TRACKING DEVICE FOR LASER EYE SURGERY USING CORNEAL MARGIN DETECTION

(75) Inventors: Ioan T. Oltean, Sunnyvale; John K. Shimmick, Belmont; Terrance N. Clapham, Jamestown, all of CA (US)

(73) Assignee: Visx, Incorporated, Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,957

(22) Filed: Oct. 6, 1998

Related U.S. Application Data

(60) Provisional application No. 60/062,038, filed on Oct. 10, 1997.

(51) Int. Cl.[7] .................................................. A61B 3/14
(52) U.S. Cl. ................................. 351/210; 606/5
(58) Field of Search ................... 351/202, 203, 351/204, 209, 210, 221, 246; 600/558; 606/4, 5; 382/115, 117; 702/2

(56) References Cited

U.S. PATENT DOCUMENTS

| | | |
|---|---|---|
| 3,804,496 | 4/1974 | Crane et al. . |
| 4,169,663 | 10/1979 | Murr . |
| 4,421,486 | 12/1983 | Baldwin et al. . |
| 4,443,075 | 4/1984 | Crane . |
| 4,579,430 | 4/1986 | Bille . |
| 4,669,466 | 6/1987 | L'Esperance . |
| 4,836,670 | 6/1989 | Hutchinson . |
| 4,848,340 | 7/1989 | Bille et al. ....................... 128/303.1 |

(List continued on next page.)

FOREIGN PATENT DOCUMENTS

| | | |
|---|---|---|
| WO 94/18883 | 9/1994 | (WO) . |
| WO 95/27453 | 10/1995 | (WO) . |
| WO 99/12467 | 3/1999 | (WO) . |
| WO 99/20173 | 4/1999 | (WO) . |
| WO 99/23936 | 5/1999 | (WO) . |
| WO 99/55216 | 11/1999 | (WO) . |

OTHER PUBLICATIONS

Young & Sheena, "Behavior Research Methods & Instrumentation", *Survey of Eye Movement Recording Methods* (1975) V7(5):401–429.

Rashbass et al. "New method for recording eye movements" Journal of the Optical Society of America (1960) 50(7):642–644.

Crane et al., "Generation–V dual purkinje–image eye-tracker" Applied Optics (1985) 24(4):527–537.

*Primary Examiner*—George Manuel
(74) *Attorney, Agent, or Firm*—Townsend Townsend & Crew LLP; Mark D. Barrish, Esq.

(57) ABSTRACT

Systems and methods derive relative eye position by tracking a boundary such as the limbus. Light can be scamed along the limbus, and measured intensity of reflected light processed to derive the eye's position.

58 Claims, 29 Drawing Sheets

U.S. PATENT DOCUMENTS

| | | |
|---|---|---|
| 4,852,988 | 8/1989 | Velez et al. . |
| 4,950,069 | 8/1990 | Hutchinson . |
| 4,973,149 | 11/1990 | Hutchinson . |
| 5,016,643 | 5/1991 | Applegate et al. . |
| 5,098,426 | 3/1992 | Sklar et al. ............... 606/5 |
| 5,162,641 | 11/1992 | Fountain . |
| 5,231,674 | 7/1993 | Cleveland et al. . |
| 5,270,748 | 12/1993 | Katz . |
| 5,345,281 | 9/1994 | Taboada et al. . |
| 5,360,424 | 11/1994 | Klopotek . |
| 5,410,376 | 4/1995 | Cornsweet et al. . |
| 5,430,505 | 7/1995 | Katz . |
| 5,471,542 | 11/1995 | Ragland . |
| 5,474,548 | 12/1995 | Knopp et al. . |
| 5,572,596 | 11/1996 | Wildes et al. . |
| 5,604,818 | 2/1997 | Saitou et al. . |
| 5,620,436 | 4/1997 | Lang et al. ............... 606/4 |
| 5,632,742 | 5/1997 | Frey et al. . |
| 5,633,695 * | 5/1997 | Feke et al. ............. 351/221 |
| 5,752,950 | 5/1998 | Frey et al. . |
| 5,782,822 | 7/1998 | Telfair et al. ............ 606/5 |
| 5,818,954 * | 10/1998 | Tomono et al. ............ 382/115 |
| 5,884,224 * | 3/1999 | McNabb et al. ............ 702/2 |
| 5,966,197 * | 10/1999 | Yee ....................... 351/210 |
| 6,022,108 | 2/2000 | Yoshida et al. ........... 351/208 |
| 6,027,216 | 2/2000 | Guyton et al. ............ 351/200 |
| 6,027,494 | 2/2000 | Frey ..................... 606/5 |
| 6,030,376 | 2/2000 | Arishima et al. .......... 606/4 |

* cited by examiner

EYE TRACKING DEVICE FOR LASER EYE SURGERY USING CORNEAL MARGIN DETECTION This application is a continuation in part of, and claims the benefit of priority from, U.S. Provisional Patent Application No. 60/062,038, filed Oct. 10, 1997, the full disclosure of which is incorporated herein by reference.

BACKGROUND OF THE INVENTION

The present invention is generally concerned with ophthalmic surgery, and more particularly relates to systems, methods and apparatus for tracking the position of a human eye. The present invention is particularly useful for tracking the position of the eye during surgical procedures, such as photorefractive keratectomy (PRK), phototherapeutic keratectomy (PTK), laser in situ keratomileusis (LASIK), or the like. In an exemplary embodiment, the present invention is incorporated into a laser ablation system which is capable of modifying the spatial and temporal distribution of laser energy directed at the cornea based on the eye's position during the laser ablation procedure.

In ophthalmic surgery, the ability to optically track or follow the movement of the patient's tissue is recognized as a highly desirable element in laser delivery systems designed to effect precision surgery in delicate ocular tissue. This tracking of the eye includes not only the voluntary movements which can be damped with specialized treatment, but also the involuntary movements which are more difficult to control on a living patient. According to Adler's Physiology of the Eye, even when the patient is holding "steady" fixation on a visual target, eye movement still occurs. Further, involuntary head motion may occur that causes further motion of the eye. Such motion may compromise the efficacy of certain ocular surgical procedures requiring great precision. This motion may occur even when total immobilization of the eye of the eye is attempted. Total immobilization of the eye is not fully effective in suppressing involuntary eye motion, is rather uncomfortable for the patient and may cause potentially sight threatening elevations in intraocular pressure. The implementation of automatic tracking of the eye would alleviate any need for such immobilization and offer a technique for more effectively accommodating all types of eye motion. Thus, augmenting surgery with a real time eye tracking system may improve upon the accuracy and speed with which surgical procedures could be performed, as well as enabling new procedures to be carried out for the first time.

Various techniques have been described for tracking eye movements. The following references disclose techniques for tracking eye movements and are herein incorporated by reference in their entirety: Rashbass, Journal of the Optical Society of America, Vol. 50, pp. 642–644, 1960; Crane and Steele, Applied Optics, Vol. 24, pp. 527, 1985; U.S. Pat. No. 3,804,496 to Crane et al.; U.S. Pat. No. 4,443,075 to Crane; U.S. Pat. No. 5,231,674 to Cleveland et al.; U.S. Pat. No. 5,471,542 to Ragland; U.S. Pat. No. 5,604,818 to Saitou et al.; U.S. Pat. No. 5,632,742 to Frey; U.S. Pat. No. 5,752,950 to Frey; PCT International Publication Number WO 94/18883 by Knopp et al.; and PCT International Publication Number WO 95/27453 by Hohla.

Many of the known tracking techniques fall into one of two distinct categories, optical point trackers and digital image trackers, the latter including numerous variations of pattern recognition and edge detection methods. Optical point trackers utilize reflected images from various layers of the eye. These trackers optically distinguish reflected light to form images such as the first, second, third and fourth Purkinje images. For example, a dual Purkinje image technique compares the displacement of two different-order Purkinje images over time, and uses a repositioning apparatus to adjust the isometric transformation corresponding to the motion. A similar application of dual Purkinje technique to stabilize a visual system was used in a fundus illumination and monitoring device. These and similar Purkinje image-based tracking methods purport to follow the movement of the anterior surface of the eye. While such techniques possess, in principle, sufficient speed to follow the displacement of Purkinje points, they include an implicit assumption that the eye moves as a rigid body. During surgery, however, the eye does not move as a rigid body. Thus, localization of the Purkinje points can be influenced by transient relative motions between the various optical elements of the eye, which leads to fictitious position information for identifying the surface of the cornea. In addition, such systems are rather complex and tend to exhibit large variability between individuals in their calibration setting, which requires continuous real-time adjustments of the amplitude of the controlling signals. Also, during surgery of the eye the optical quality of the eye is temporarily degraded. This temporary degradation of the optical quality distorts and blurs the Purkinje images. Therefore, these blurry images make an accurate determination of the position of the eye very difficult.

Another class of tracking methods involve, in one form or another, digital image processing techniques. These techniques include retinal image trackers, various pattern recognition algorithms and edge detection techniques. In these cases, very fast frame-rate CCD cameras, sophisticated processing algorithms, and high speed computer processing are required along with fast servo-controlled mirrors for closing the loop. These requirements are generally caused by the large amounts of digital data produced by images used for image processing and the computational requirements for processing images. With the frequency response limited in practice to about one tenth the update frequency, digital image comparisons are considered to be relatively slow. In the case of tracking eye motions, setting the sampling frequency to an order of magnitude higher than the highest frequency to be pursued translates into kHz rates, leaving less than one thousandth of a second for processing the signal information.

Several other practical difficulties plague most image processing techniques including the need for rather prominent and recognizable features, which are often not easily located in the eye's structures during surgery. Also, techniques predicated upon high speed image processing of video signals are often deficient due to unfavorable tradeoffs between field of view, spatial resolution and frequency response. Specifically, since the image processing algorithms are limited by the size and spacing of the view elements (pixels), the digital methods do not afford continuous resolution. Increasing the resolution exacts penalties in terms of the field of view. Yet, relatively large areas should be acquired. One approach is to increase the number of pixel elements in an image sensor. Unfortunately, increasing pixel resolution significantly increases the system cost and degrades the system frequency response because of increasing image data and computations. Alternatively, fast moving optical deflectors and associated control circuitry may be employed. Unfortunately, this additional instrumentation also increases system cost and degrades the system response time. Consequently, the system will have an undesirable combination of diminished resolution, decreased response time or increased cost.

A more promising technique for tracking eye movement takes advantage of the differences in the light scattering properties of the iris and sclera. In this technique, light is projected onto the cornea/sclera interface or limbus, and the scattered light from the limbus is detected by photodetectors to determine an edge or boundary of a portion of the sclera and cornea. With this technique, the iris beneath the cornea will absorb light passing through the cornea and make the cornea adjacent the sclera appear dark. The relative position of this boundary can then be monitored to track the position of the eye.

The prior art techniques for tracking a boundary such as the limbus lack the desired combination of accuracy, speed and affordability that would be desirable for use with laser eye surgery. One technique of tracking the boundary of the cornea and sclera has been to project a single spot onto a portion of the limbus and vary the position of the spot along a line such that the light reflected onto a detector remains constant. The position of the projected spot is then assumed to represent the position of the limbus. Unfortunately, measurements which are taken of a portion of an object such as a single spot projected onto the limbus do not accurately represent the position of the entire object. A further disadvantage of tracking a single spot is that the portion of the limbus that is tracked may not be clearly visible or may change during surgery.

A further technique for tracking the limbus has been to utilize position sensing detectors, and offset a mirror to aim the element at a new offset position of the eye. These additional electronics typically involved with these techniques can increase the cost of the system and can decrease the system response time. Various factors also limit the effectiveness of this approach, particularly its sensitivity to individual variability among eyes, such as variations in iris diameter and varying contrast between the iris and sclera. Further, systems using this approach will typically only sample a limited portion of the limbus, and this portion of the sampled boundary may be covered by tissue during surgery.

Another problem with existing eye tracking systems which measure the position of the limbus occurs when the limbus is covered by tissue during surgery. An example of a surgical procedure that covers a portion of the limbus is laser in situ keratomileusis (LASIK). During this procedure, the epithelium, Bowman's membrane, and a portion of the anterior stroma are partially incised from the stroma and folded back to expose the stroma to the laser. The partially removed corneal tissue is typically folded back away from the center of the cornea and laid over a portion of the limbus. The incised tissue covering the limbus, however, is extremely rough and a poor optical surface. Accordingly, systems that rely on light reflection or scattering from this region of the eye do not provide meaningful data. Further, the position of the flap may vary among surgeons. This variability of flap position can cause further problems with prior art eye trackers. For example, a surgeon may not be able to perform LASIK as desired because his or her preferred orientation of the flap of incised tissue may cover a portion of the eye used by the eye tracker.

Laser surgery systems that have been integrated with eye trackers in the past have used the eye tracker to provide a central reference.

The performance of these integrated surgical laser and eye tracking systems is often less than optimal when used with the LASIK surgical procedure. With the LASIK surgical procedure, the central features of the cornea and underlying tissues are not easily located because of the rough corneal surface produced by the incision. Further, the laser treatment may change the corneal tissue and make tracking more difficult by changing the visibility of a tracked feature.

Another limitation of the prior art eye trackers has been the algorithms employed for coupling the offsetting of the laser beam to match the eye motion. For example, some systems repeatedly adjust an aiming beam toward an intended target until the two positions are aligned. This repeated adjustment of the laser beam will delay the laser treatment. Laser treatment delays are undesirable because they can cause the drying of the eye and too much tissue to be removed from the dried eye.

What is needed therefore are improved methods and apparatus for tracking the eye. In particular, these methods and apparatus should be capable of accurately tracking eye movements in real time so that these movements can be compensated for during, for example, a laser ablation procedure. It would be particularly desirable if these methods and apparatus could be used during procedures in which a portion of the outer reflective surface of the eye (i.e., the epithelium, and/or the anterior corneal tissue) is variably removed, such as in LASIK procedures. Further, it would be desirable if these eye tracking techniques were optimally integrated with a surgical laser system.

SUMMARY OF THE INVENTION

The present invention is directed to systems, methods, and apparatus for tracking the relative position of the eye. The present invention is additionally directed to systems, methods and apparatus for laser sculpting an eye to a predetermined shape by photo-ablation while tracking the relative position of the eye. In particular, the techniques of the present invention derive the position of the eye by tracking the interface between the white cornea and the colored iris (i.e., the limbus). The limbus, located at the outer edge of the cornea, presents several advantages as a tracking landmark for corneal procedures. For example, the limbus is contiguous to the targeted corneal tissue and is expected to provide a faithful representation of nonsurgically induced displacements. Yet it is located far enough from the site of operations so that the transient displacements occasioned by the impact of the laser pulse on the target site will be damped sufficiently to avoid inducing fictitious tracking signals.

By contrast with either image processing based systems or optical point trackers, the systems and methods of the present invention involve contrast tracking which does not rely on well-defined edges and/or patterns. In one aspect of the present invention, a method for tracking the movement of the eye of patient comprises directing light to an annular region of the eye between the sclera and the iris and receiving reflected light from that region. The intensity of the reflected light is then measured to determine a relative position of the eye. In some embodiments, an annular light pattern is directed onto a region of the eye radially outward from the pupil. In other embodiments, a light spot is scanned around a substantially annular trajectory radially outward from the pupil. The signals corresponding to the intensity of the reflected light are then processed and measured to determine the eye's position relative to the annular pattern or trajectory. Preferably, the annular light pattern or trajectory will be wide enough to include both the sclera and the iris (i.e., wider than the limbus transition region). Since the light reflected from the sclera has a higher intensity than the light reflected from the iris, the total surface area of the sclera and iris within the light spot can be determined to compute the relative position of these two regions of the eye.

In a specific configuration, a light spot is scanned around an annular trajectory substantially coincident with the limbus between the sclera and the iris (which could have different shapes for different patients). The light trajectory is adjusted so that it is substantially concentric with the limbus at the beginning of the procedure. An alternating current component of the same frequency as the light spot frequency is generated as a reference signal. The amplitude of the light spot signal can be compared with the amplitude of the reference component to determine the magnitude of eye displacement, and a phase of the light spot signal can be compared with a phase of the reference component to determine a vector angle of the eye displacement. For example, if the eye is rotated laterally with respect to the annular trajectory, light reflected from one side of the annular trajectory will have a higher intensity because the sclera will occupy most or all of the annular trajectory in this region. The intensity from the other side of the trajectory will be much lower because the iris will occupy most, if not all, of this region of the trajectory. Thus, the amplitude of the frequency signal will increase above the reference intensity signal as the light is scanned on the side of the eye containing mainly the sclera. The frequency signal will then decrease below the reference intensity signal as the light beam travels to the other side of the limbus containing mostly the iris. The resulting sinusoidal signal can be compared with the reference signal to determine both the magnitude and displacement vector of the eye.

The light may be scanned around the annular trajectory using a variety of different techniques. In one embodiment, light is transmitted from a light source through one or more optical fibers to the eye. The optical fibers include a proximal transmit section coupled to the light source and a distal transmit/receive section positioned in front of the eye. The distal region may be rotated around a substantially annular trajectory such that the light scans around the eye along this trajectory. Likewise, the light is then received by the distal region and passes through to a second proximal fiber section (which can be the same or a different set of fibers as the transmit fibers). The light is received by a light detector, such as a phototransistor, a CCD, or the like, and the corresponding signals are processed to generate an oscillating analog signal representing the position of the eye.

In another embodiment, the light direction system includes a ring of light sources positioned around the eye in a line with the annular track. The light sources are sequentially activated so as to "scan" light around this annular track. Alternatively, the light sources may be activated simultaneously such that an annular light pattern is directed onto the eye. The annular light pattern can be measured as a whole to determine the eye position, or each light source may have a corresponding photodetector that measures the intensity of the individual light beams. In another embodiment, the light direction system includes one or more oscillating mirrors, e.g., galvanometer mirrors, positioned between a light source and the eye to scan the light around the limbus.

In another aspect of the invention, systems and methods are provided for tracking relative position of the eye during a surgical procedure, such as photorefractive keratectomy (PRK), phototherapeutic keratectomy (PTK), laser in situ keratomileusis (LASIK), or the like. During the laser ablation procedure for PRK, the epithelium is removed to expose the underlying Bowman's layer of the cornea. In LASIK procedures, the epithelium, Bowman's membrane and a portion of the anterior stroma are partially incised from the stroma and folded back to expose the stroma to the laser. An ultraviolet or infrared laser is employed to remove a microscopic layer of anterior stromal tissue from the cornea to alter its refractive power. According to the present invention, the relative position of the limbus is tracked as described above, and the laser beam is modulated to compensate for movement of the eye.

The present invention is particularly useful during LASIK procedures because the light trajectory passes above and below the region of tissue that has been folded or removed from the eye. The light passing through the portion that has been incised will generally provide little information regarding the position of the limbus. However, since the light trajectory is a known shape (i.e., a circle, oval, etc) the entire trajectory can be interpolated from the information obtained from the upper and lower regions.

In yet another embodiment of the invention, the invention provides a method of tracking a position of an eye having a boundary such as the limbus. The method includes directing a light energy at the eye and measuring an intensity of the energy reflected from a region of the eye. The region includes a portion of the boundary. By scanning the measured region around the eye, the position of the eye is determined from a variation in the intensity of the reflected energy.

In some embodiments, the size of a dimension across the measured region is restricted by selectively passing light rays from within the region to a light energy detector, and excluding light rays from outside the region from the light energy detector. Rotating the measured region around the eye at a reference frequency generates a varying signal at the reference frequency. Comparing an amplitude of the varying signal with a reference can determine a magnitude of an eye displacement. Comparing a phase angle of the varying signal with the reference can determine an angle of the position of the eye. The method may further include positioning the trajectory to be substantially coincident with the boundary, and adjusting a radius of the trajectory to match a radius of the limbus.

In a further embodiment of the invention, the invention provides a method of tracking a position of an eye having a boundary by projecting a beam of light energy at the eye and measuring an intensity of the energy reflected from a region of the eye. The region includes a portion of the boundary and is aligned with the beam. By scanning the beam and the region around the eye, the position of the eye is determined from a variation in the intensity of the reflected energy.

Optionally, the size of a dimension across the measured region can be restricted by selectively passing light rays from within the region to a light energy detector and excluding light rays from outside the region from the light energy detector. Rotating the measured region around the eye at a reference frequency may optionally generate a varying signal at the reference frequency.

In a yet further embodiment of the invention, the invention provides a method for tracking a position of an eye that includes projecting a light beam from a display onto the eye and measuring an intensity of the energy reflected from a region of the eye. The region includes a portion of the boundary. By scanning the beam around the eye, a position of the eye is determined from a variation in the intensity of the reflected energy.

In yet another aspect, the invention provides a method for tracking a position of an eye during surgery. The eye has a limbus, and the method comprises directing a light energy at the eye. An intensity of the energy reflected from a region of the eye is measured, the region including a portion of the limbus. A flap of excised tissue covering the limbus is automatically detected.

In still another embodiment of the invention, the invention provides a method of treating an eye with a beam of a laser treatment energy comprising automatically detecting an excised flap of tissue covering the limbus of the eye. The method also includes directing a light energy at the eye, measuring an intensity of the light energy reflected from a region of the eye, and applying the treatment energy to a tissue structure on the eye.

In still another embodiment of the invention, the invention includes an eye tracker for measuring a position of an eye having a boundary, and the tracker includes a controller coupled to a light detector for automatically detecting a tissue covering the boundary. The controller measures the reflected light energy from an uncovered portion of the boundary to determine a relative position of the eye. The embodiment also includes a light source for making a light energy, a light detector positioned to receive the light energy reflected from a region of the eye, and an optical train for scanning the region over the eye. The embodiment may also include a blanking circuit for blanking a projected visible light spot over the detected tissue covering the boundary, an interpolation circuit for interpolating the measured light energy, and an offset circuit for displacing the annular trajectory to match the position of the eye.

In another additional embodiment of the invention, the invention includes a laser surgery system integrated with an eye tracker. The system includes a laser for generating a beam of an ablative laser energy, and a movable laser beam path that is variably offset from a reference position. The eye tracker includes a movable eye tracker axis. The eye tracker axis is movable so that a position of the eye tracker axis matches a position of the eye. The eye tracker axis is independently movable relative to the movable laser beam path. A laser system controller offsets the laser beam path according to a position of the eye tracker axis and value of a laser treatment table.

In light of the above, it is an object of the invention to quickly and accurately measure the position of an eye by measuring a boundary of the eye.

DESCRIPTION OF THE PREFERRED EMBODIMENT

Figure 1:
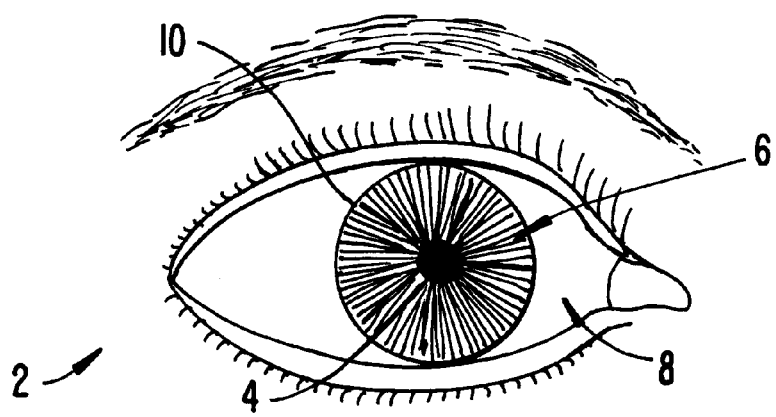
FIG. 1 is a front view of the surface anatomy of the eye, illustrating the contrast between the iris and the sclera.

The present invention is directed to systems, methods, and apparatus for tracking the relative position of the eye. In particular, the techniques of the present invention detect the contrast in recognizable large scale boundaries such as the cornea/sclera interface (limbus) to determine the location and orientation of these boundaries, often without having to resort to image processing techniques. Although the limbus is the preferred boundary, one skilled in the art will recognize that other boundaries (such as the edge of the pupil/iris interface) may be tracked with the techniques of this invention. In preferred aspects, the cornea/sclera interface is tracked with a light spot that is scanned around an annular trajectory to provide an oscillating signal that indicates the magnitude and displacement of the limbus from a reference position. For corneal procedures, including refractive surgery, the eye limbus at the radially outward edge of the cornea provides sufficient contrast to allow the employment of the tracking methods discussed in this invention. In addition, the limbus has the advantage of not only moving with the cornea—inasmuch as it is a part of the cornea—but, since it likewise is connected to the sclera, it will not respond as dramatically to the transient deformations associated with refractive surgery.

The invention often includes directing light energy at the eye. The light energy will be directed toward the eye as a beam of light energy. The intersection of the beam of light energy with the eye will comprise a light spot formed on the eye.

Various techniques may be used to define a measured region that may be scanned over the eye. In one embodiment, a projected spot of light energy may be used to define the measured region. The measured region may be scanned over the eye by scanning the projected spot. In another embodiment, an aperture defines the measured region by restricting an area on a surface of the eye that can reflect light energy from the measured region to a light energy detector. In other embodiments, the measured region is defined by projecting a light spot onto a restricted area of the eye, and the restricted area is further defined by selecting light rays from the restricted area and excluding light rays from outside the restricted area.

While the exemplary embodiments of the present invention will herein be described with reference to systems having analog signal processing circuitry, digital data processors, and in particular, combinations of analog and digital components, it should be recognized that the present invention encompasses (and provides advantages for) tracking systems and methods which are more digital (or even exclusively digital) in nature. As digital processors become increasingly capable (particularly for image processing), faster, and lower in cost, and as optical digital electronic interface components (for example, CCD sensors, flat panels and other selective illumination arrays, image capture and analysis systems, and the like) improve in response time and resolution, some or all of the analog components may, now or in the future, be replaced with digital hardware, software, or a combination of hardware and software. Similarly, more predominantly analog systems might also be made, or even systems making use of optical signal manipulations. Hence, those of skill in the art of digital signal processing will understand that digital computer processing systems may augment or substitute for the structions and functions illustrated and described herein with reference to analog components.

Referring to FIG. 1, the surface anatomy of a human eye 2 is illustrated. As shown, the eye 2 includes a pupil 4 in the center, surrounded by a darker iris region 6. The iris 6 is surrounded by the white sclera 8 covered with a transparent mucous membrane or conjunctiva. The transparent cornea 12, through which light enters the eye, bulges anteriorly from its junction with the sclera 8 (see FIG. 2). The iris 6 is the visible colored part of the eye which lies between the cornea 12 and the lens 14 and its round central opening, the pupil 4, allows light to enter the eye. Although irises come in many colors, they will generally reflect light at a particular intensity. The sclera 8 is the white portion of the eye that generally reflects light at a greater intensity than the iris 6. The region interfacing the cornea and sclera, typically referred to as the limbus 10. This region is a substantially annular region that provides a high contrast between the sclera 8 and the cornea 12. This high contrast may generally be attributed to the light absorbing iris 6 underlying cornea 12, which absorbs the light passing through cornea 12.

Figure 1A:
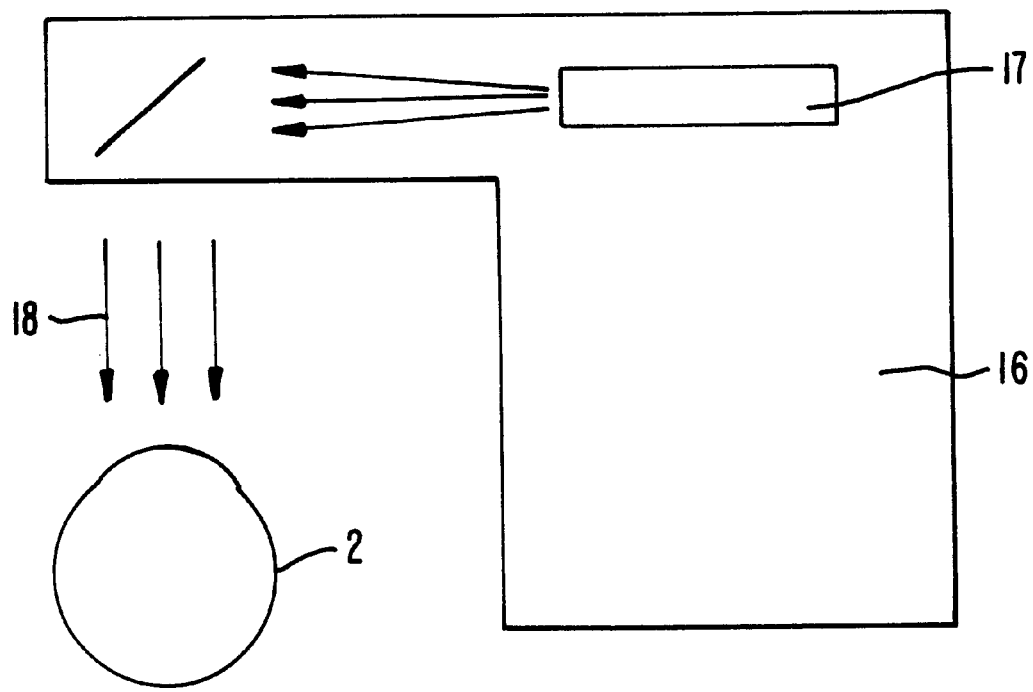
FIG. 1A is a schematic view of a laser surgery system for incorporating the invention.

Referring to FIG. 1a, this figure schematically illustrates a surgical laser system 16. The laser surgery system 16 includes a laser 17 for generating a beam 18 of laser energy. The eye 2 is positioned under the laser surgery system 16 for treatment with a beam 18 of laser energy. The eye 2 is desirably aligned with the laser surgery system 16 prior to treating the eye with the laser beam.

Figure 2:
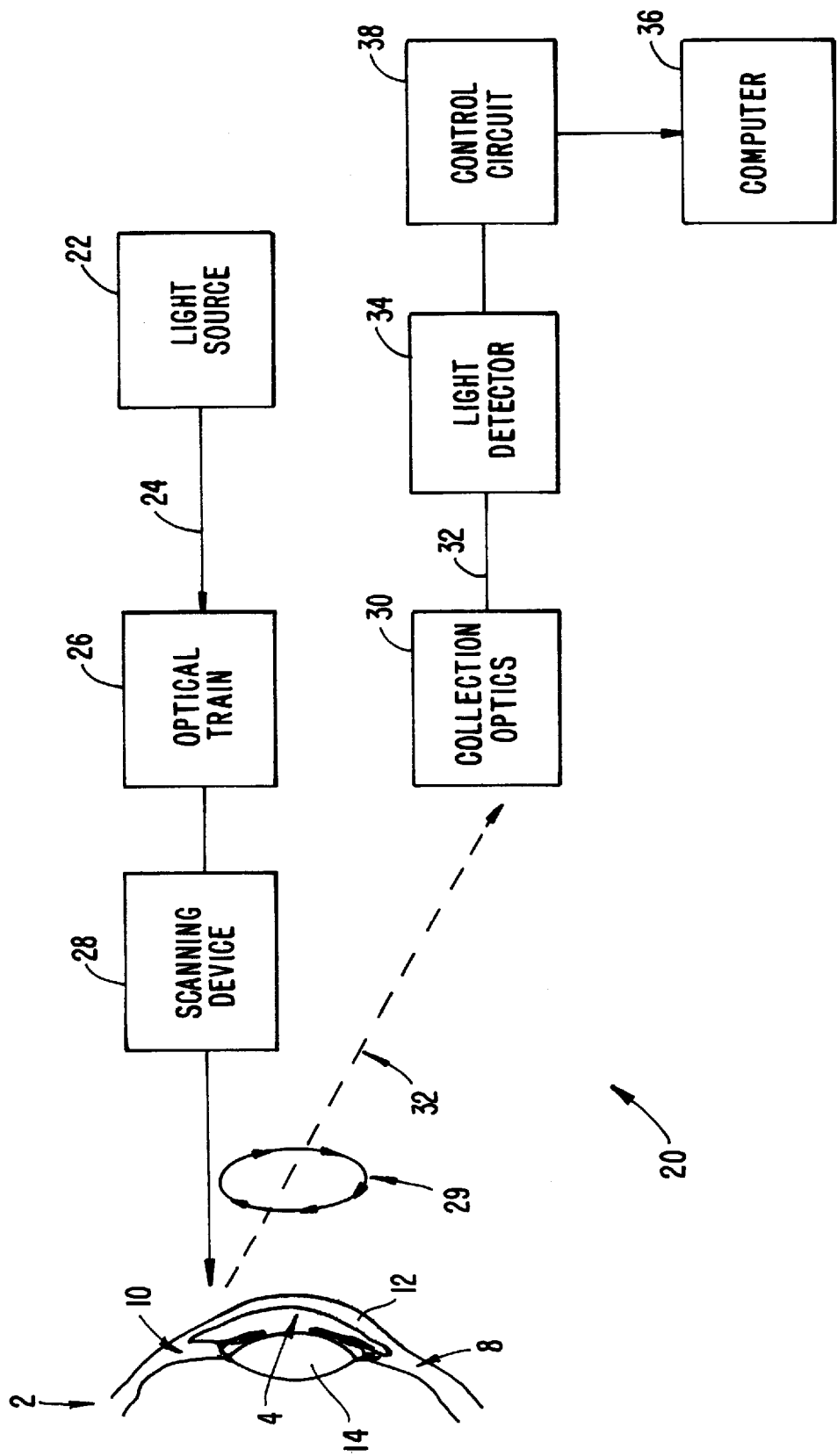
FIG. 2 is a block diagram of the basic components of the optical system and method of the present invention.

Referring to FIG. 2, an optical system 20 for projecting light onto the limbus 10 to measure reflected light from the region to track eye movement is schematically illustrated according to the present invention. Optical system 20 generally includes a light source 22 for directing a single or a plurality of light rays 24 through an optical train 26 onto the limbus 10 of the eye 2. The optical train 26 will include a light direction apparatus 28 for scanning or sequentially projecting light rays 24 around a trajectory 29 that coincides with (at least initially) the limbus 10. Alternatively, light source 22 and optical train 26 may be configured to direct a light pattern onto the limbus 10. The light rays 24 are scattered from the eye through collection optics 30 (which may be part of the optical train) which refocus the scattered light 32 onto a light detector 34 to form the measurable signals.

The system will preferably include filters (not shown) in the optical train 26 and/or collection optics 30 to filter spurious light. These filters are generally transmissive to radiation in the wavelength of the light source while reflective to radiation at other wavelengths. This helps to separate the light rays projected onto the limbus of the eye from other light sources in the operating room. A computer 36 and a control circuit 38 are in electrical communication with detector 34 to process the corneal margin signals and to measure the relative magnitude of the eye displacement.

Figure 3:
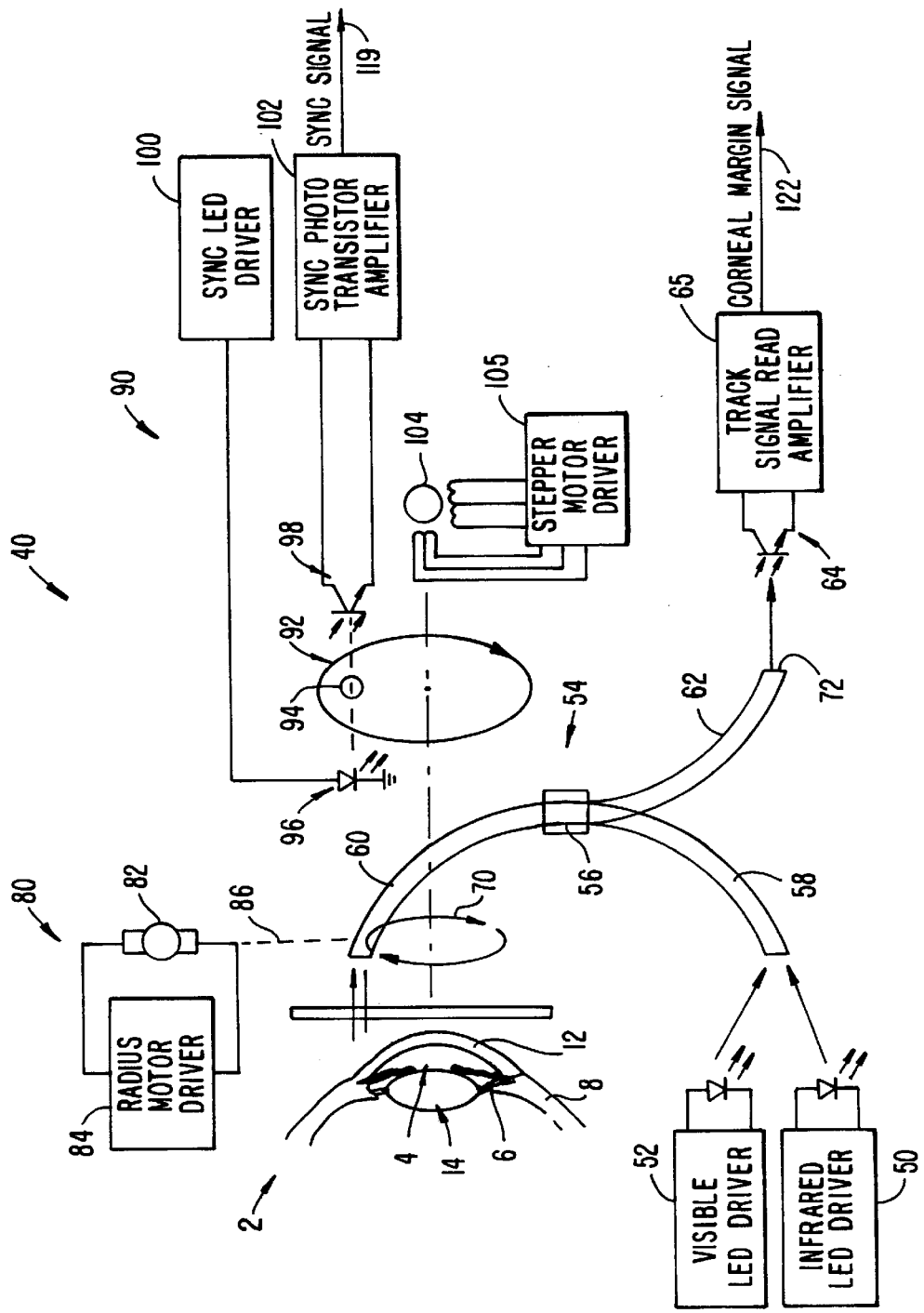
FIG. 3 is a functional block diagram of an optical system for tracking the boundary between the iris and the sclera according to one embodiment of the present invention.

Referring now to FIG. 3, one embodiment of the present invention will be described in detail. As shown, an optical system 40 comprises a light source 50, which is activated by a power supply (not shown) to pass light rays through a Y-shaped optical fiber 54 to the eye. The light source 50 may comprise one or more light sources, e.g., laser, such as argon, helium-neon and diode lasers, or the like, halogen light sources, light emitting diodes, and the like. In one embodiment, the light source 50 will emit light having a red to near infrared wavelength, about 700–900 nanometers. This wavelength range has the highest sensitivity for many detectors and it also allows the optics to filter light from other sources, such as a microscope viewing light or the like from the operating room (which is typically in the 400 to 700 nanometer range). The infrared light source 50 may be configured to directly emit such wavelengths, e.g., light emitting diodes, or it may be equipped with one or more filters (not shown) that only transmit wavelengths within the red to near infrared range. Alternatively or additionally, the system may include a visible light source 52 that emits a visible wavelength to produce a visible ring of light at the limbus that might be useful for other purposes (e.g., initial calibration of the light trajectory onto the limbus). Since the systems and methods of the present invention avoid shining light directly through the opening of the iris, they are generally safe to the retina.

Optical fiber 54 includes a proximal transmit section 58 optically coupled to light sources 50, 52 for transmitting light rays through a common trunk 56 to a distal transmit/receive section 60, which is suitably configured to transmit the light rays onto the limbus 10 of the eye. The distal transmit/receive section 60 of the fiber is rotated in a circular fashion with its end kept constantly on an annular trajectory 70 through the use of a suitable mechanical bearing (not shown). Optical fiber 54 further includes a receive section 62 coupled to distal section 60 for guiding the scattered light to a phototransistor 64. Optical fiber 54 includes dedicated transmit and receive multiple fiber sections in common trunk 56 with the individual fibers belonging either to the transmitter or receive sections or being randomly intermixed. The trunk 56 of the composite fiber 54 can be as long as necessary and is quite flexible. The receive fibers are situated to capture the scattered light from the eye and to guide the light to a receive fiber end 72. The scattered light rays pass through fiber end 72 and impinge upon a photosensitive surface of a phototransistor 64, which converts the light into electrical signals. A read amplifier 65 amplifies the corneal margin signal 122 and forwards the signal 122 to an electrical system 120 (see FIG. 4), as discussed below.

A synchronous stepper motor (not shown) may be used as the drive for spinning the end of distal fiber section 60 around trajectory 70, although other suitable drives may be used with the present invention. In addition, a second drive may be used to initially calibrate the spin trajectory of the optical fiber so that it is concentric with the limbus 10 of the eye (further details of this method are discussed below). In one embodiment, this calibration drive includes a radius motor drive 80 having a high ratio mechanical reductor, such as a worm gear 82, and a mechanical coupling 86 for coupling a DC motor 84 to the end of the optical fiber 60. When the desired radius is achieved, the DC motor 84 can be removed and the worm gear 82 will maintain the radius constant during the procedure.

As shown in FIG. 3, optical system 20 may further include a reference signal system 90 that generates a reference synchronization signal 119 for comparison with the signals produced from the optical fiber 54. In one embodiment, reference signal system 90 includes a timer disk 92 having a hole 94 at its perimeter, and a light source, such as an LED 96, for shining light through the hole 94 in the rotating disk 92 to a phototransistor 98. As shown, reference signal system 90 includes a synchronized LED driver 100 and a synchronized phototransistor amplifier 102 coupled to phototransistor 98. A spin motor 104 having a stepper motor drive 105 is coupled to the timing disk 92 for rotating the timing disk at a reference synchronization frequency.

Figure 4:
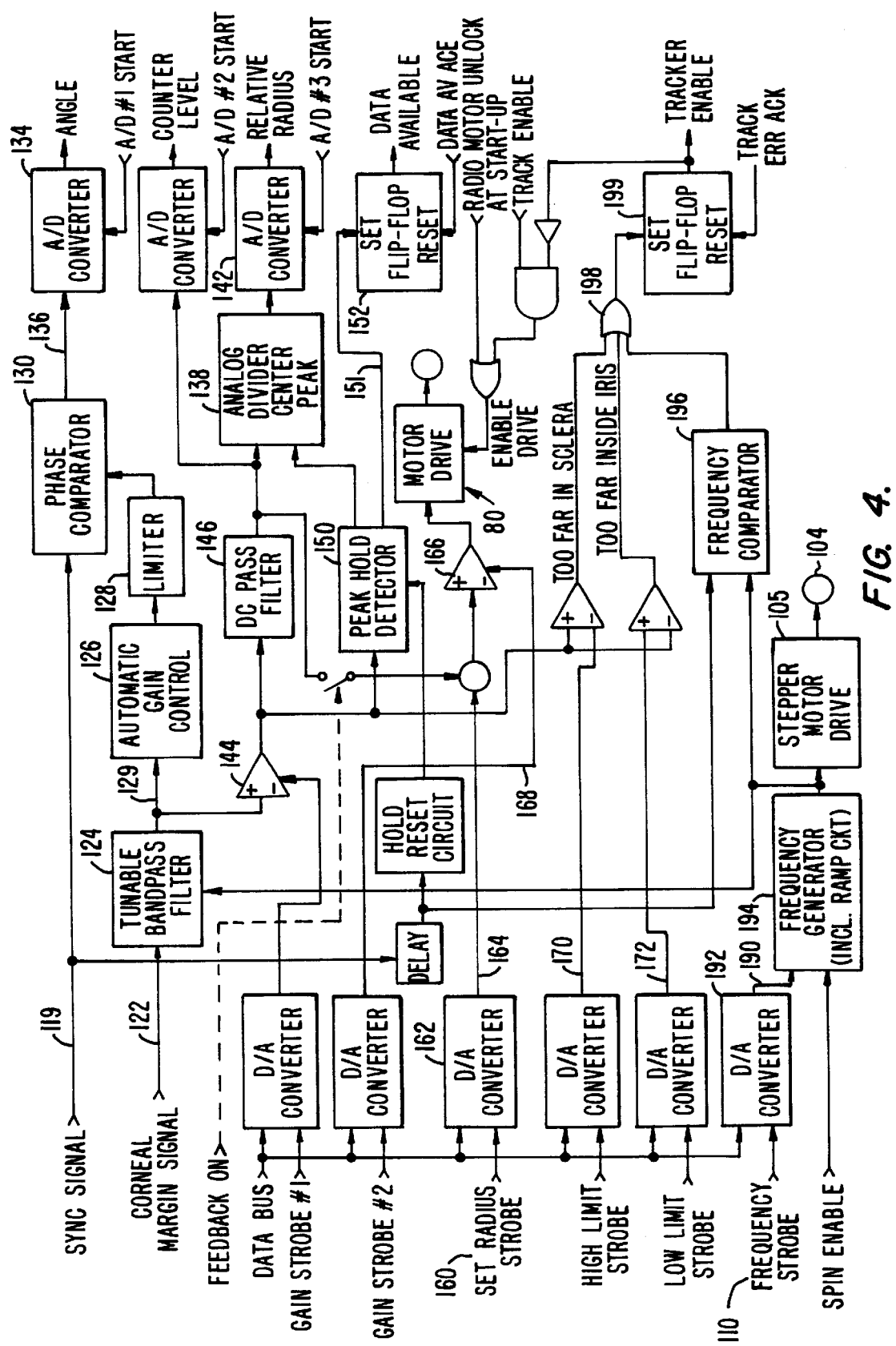
FIG. 4 is a block diagram of a control circuit for determining the magnitude/phase polar coordinates of the eye center based on the signals received from the optical system of FIG. 3.

Referring to FIG. 4, an electrical system 120 for receiving and processing the reference and corneal margin signals 119, 122 from optical system 20 is illustrated. It will be appreciated that conversion of the light pattern to electric signals by phototransistors 64, 98 effectively constitutes handover from the optical to the electronic subsystem. As shown, a first input into electrical system 120 is the corneal margin signal 122 received from phototransistor 64. In order to improve the signal to noise ratio, the corneal margin signal 122 is preferably filtered using a programmable band pass filter 124 tuned to the spinning frequency. Alternatively, the infrared LED driver 50 may be pulsed at a specific known frequency and the programmable bandpass filter tuned to the specific frequency of the LED driver. After being amplitude stabilized and limited by an automatic gain control 126 and a limiter 128, respectively, the filtered signal 129 is applied as one input into a phase comparator 130. The second input to phase comparator 130 is the reference synchronization signal 119 from the timing wheel 92 on the spinning motor shaft. The output of the phase comparator 130 is a relative angle of the eye displacement 136, which is digitized in an A/D convertor 134 for further processing.

The filtered corneal margin signal 129 is used to measure the relative magnitude of the eye displacement by dividing the peak amplitude of the AC component (at the spinning frequency) by the value of the DC component, using a divider 138. Specifically, the filtered corneal margin signal 129 and a gain are input into an operational amplifier 144, filtered through a DC pass filter 146 and then input into divider 138. The output of operational amplifier 144 is also input into a peak detector 150, which outputs the peak amplitude into divider 138. The output of divider 138 is a signal 140 representing the relative magnitude of the eye displacement, which is digitized by an A/D converter 142 for further processing.

In order to maintain flexibility, all gains and set points of the tracking system are preferably programmable by digital to analog converters under user control. The "Peak Captured" signal 151 provided by peak detector 150 is sent to a flip-flop 152 that indicates that angle and magnitude data are ready to be transmitted to the user. A reference magnitude is a user programmed voltage that achieves the desired spinning radius when the user manually adjusts the radius using a visible light spot and views the spot trajectory through a wide field microscope (not shown). Specifically, a radius set point 160 can be programmed by the user and input into electrical system 120 via a D/A converter 162. The desired radius 164 of the light trajectory may be adjusted, for example, by scanning a visible light spot on the eye until the visible light trajectory is substantially coincident with the limbus 10. The desired radius 164 is input into an operational amplifier 166 with a gain 168, and the output of operational amplifier 166 is applied to radius motor drive 80. A position feedback system may be provided to keep the radius constant after achieving a satisfactory lock on the corneal margin. In other embodiments, the spot trajectory may remain under the control of the digital processing system before, during, and after lock.

Protection and diagnostic circuits may also be provided for the supervision of the minimum and maximum spinning radius limits and for malfunctions of the spinning motor and associated drive circuitry. For example, the user may input upper and lower limits 170, 172 on the trajectory radius. A desired frequency 190 of the light trajectory may also be input via a D/A converter 192 into a frequency generator 194. The frequency generator 194 is suitably coupled to stepper motor drive 105 for spinning timer disk 92 at the desired frequency 190. As shown in FIG. 4, the desired frequency 190 can be compared with the actual frequency of the reference signal in a frequency comparator 196. An OR gate 198 is coupled to a flip-flop 199 for setting or resetting the optical system 40 if the trajectory is too far into the sclera or iris (outputs of the upper and lower radius limits 170, 172), or if there is an error in the desired frequency from comparator 196.

Tracking is initiated and stopped upon commands issued by a CPU (not shown). Since the CPU comprises, typically, a digital VME based bus, it is understood that provisions are included to issue the start/stop tracking commands in digital format. In addition, when the tracker of the present invention is part of a larger system, the CPU provides an essential link for interfacing with other assemblies such as an axial trajectory or a target viewing system. As described above, alternative tracking structures might rely to a greater extent on digital illumination, sensing, and signal processing components.

Figure 5:
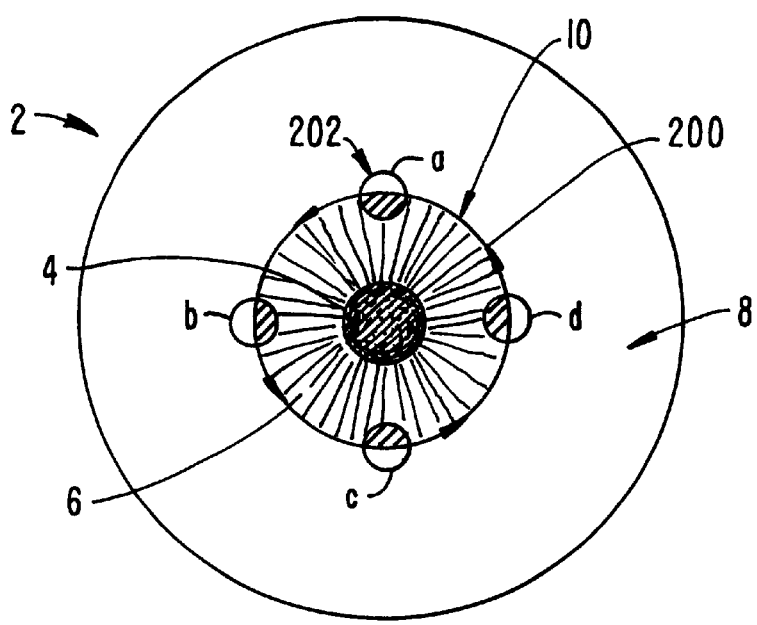
FIG. 5 is a schematic view of a light spot scanning around the iris/sclera boundary, illustrating the case in which the optical axis of the eye is aligned with the optical system.

Referring to FIG. 5, a method for tracking a human eye during a surgical procedure will now be described. The present invention may be used in conjunction with a wide variety of surgical procedures on the eye, and is particularly useful with laser ablation procedures, such as photorefractive keratectomy (PRK), phototherapeutic keratectomy (PTK), laser in-situ keratomileusis (LASIK) or the like. In such procedures, a laser is prepared to deliver the appropriate radiation in accordance with the calculated beam delivery parameters for the specific procedure, e.g., the power level and spatial location on the corneal surface. In PRK or PTK procedures, the epithelium is completely removed to expose the anterior region of the stroma. In LASIK procedures, the epithelium, Bowman's membrane and a portion of the anterior stroma are partially incised from the stroma and folded back to expose the stroma to the laser. The laser beam is typically controlled to impinge upon an area of the cornea of an eye to form therein a predetermined ablation shape. The laser selected for use preferably emits in the ultraviolet, namely at wavelengths of less than substantially 400.0 nm. Further details of suitable system and methods for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,683,379 and 5,163,934, the complete disclosures of which are hereby incorporated herein by reference.

Figure 6:
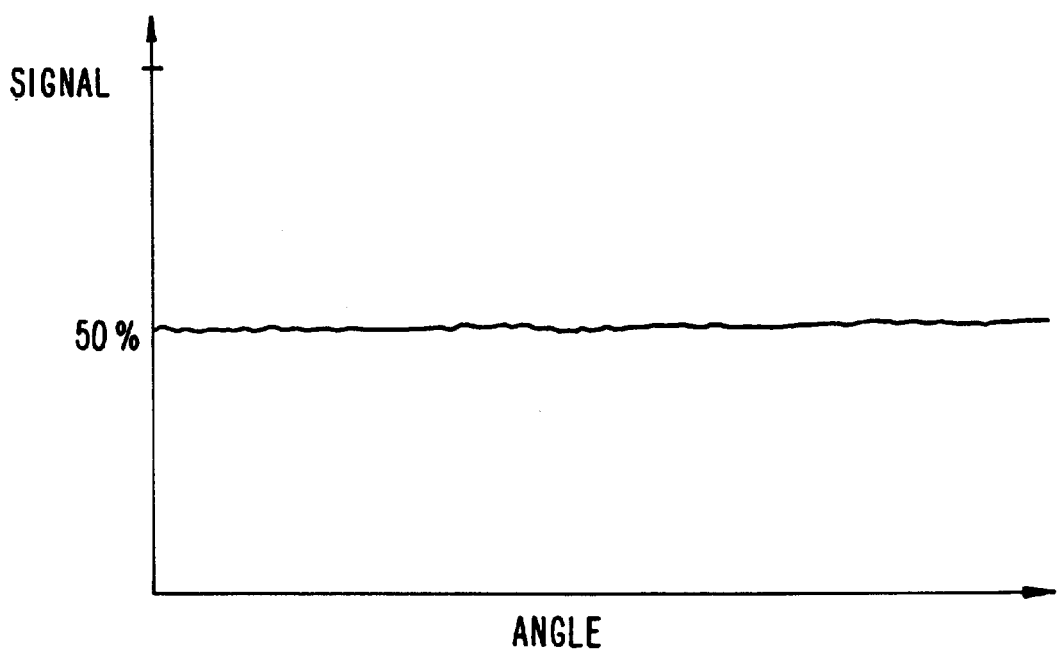
FIG. 6 is a graph illustrating the signals received by the control circuit of FIG. 4 in the case of FIG. 5.

As shown in FIG. 5, the system is initially calibrated by adjusting the radius of the spot trajectory 200 using a visible light spot 202 and scanning the light spot around the eye 2. When the light spot 202 is scanning around a trajectory that substantially coincides with the limbus 10 of the eye, the system locks this trajectory to provide a reference trajectory in which the relative position of the eye will be measured from. As shown in FIG. 6, if the light trajectory 200 is exactly coincident with the limbus 10 of the eye, a substantially constant intensity signal should be produced with electrical system 200. This is because the intensity of the light scattered from the eye does not change substantially as it passes along the trajectory (each point on the trajectory will generally have the same amount of sclera and the same amount of iris therein, which will produce a generally constant intensity signal). Of course, it will be recognized that this intensity signal will not be exactly constant as the reflectivity of the eye (including the limbus) varies spatially. In addition, it is difficult to align the light trajectory so that it is exactly coincident with the limbus 10, and the width of the limbus may vary around its perimeter. However, these variances can generally be taken into account when calibrating the system.

Figure 7:
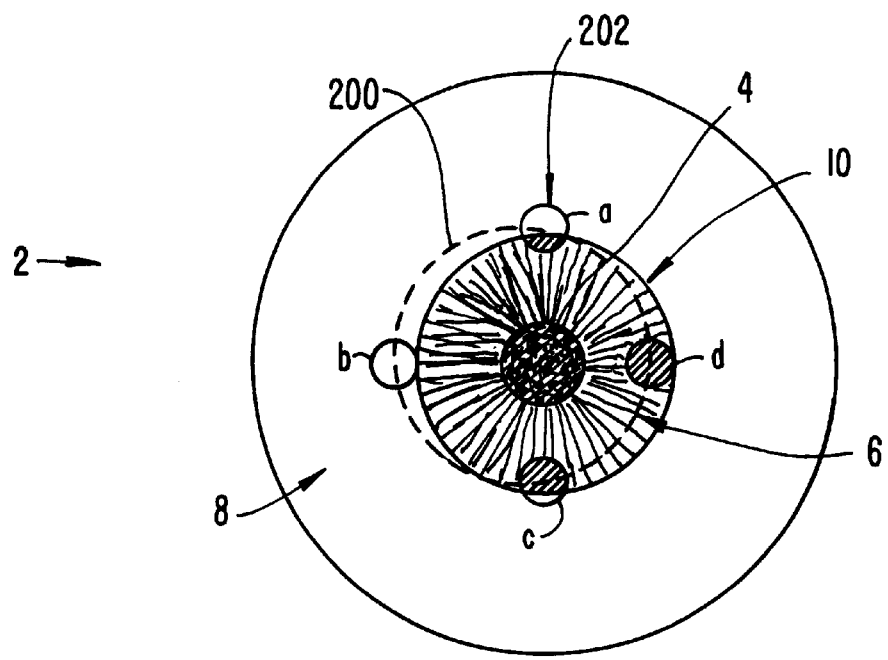
FIG. 7 is a schematic view of a light spot scanning around the iris/sclera boundary, illustrating the case in which the optical axis of the eye is not aligned with the optical system.
Figure 8:
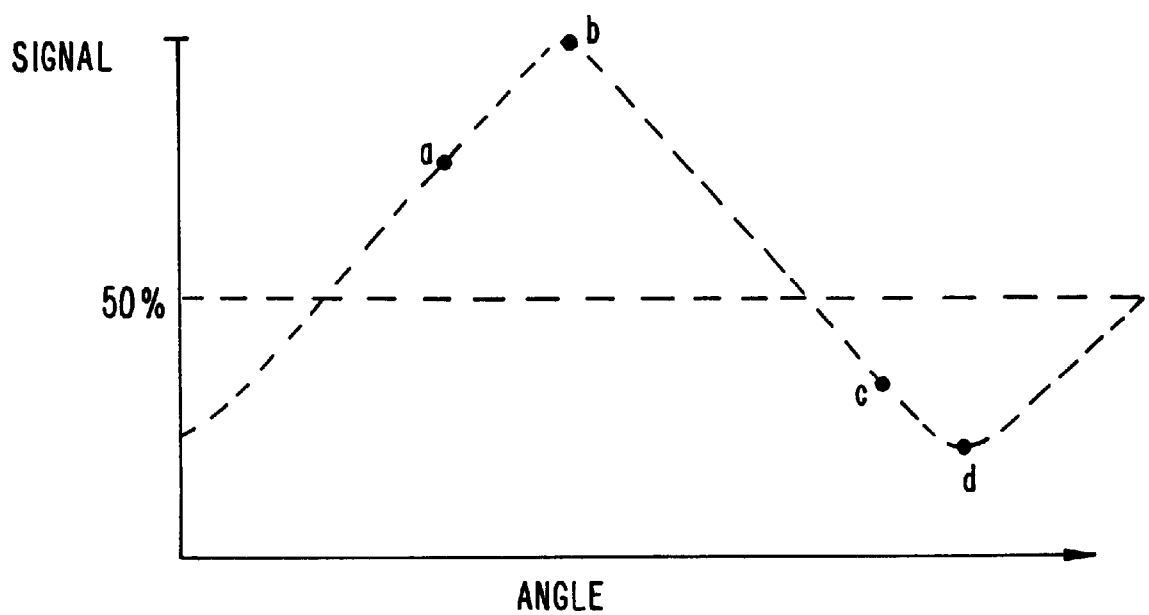
FIG. 8 is a graph illustrating the signals received by the control circuit of FIG. 4 in the case of FIG. 7.

Referring to FIGS. 7 and 8, when the patient's eye moves, the limbus 10 will no longer be aligned with the spot trajectory 200. For example, FIG. 7 illustrates this misalignment when the eye rotates laterally relative to the spot trajectory 200. At position A, the light spot 202 is positioned such that it covers more of the white sclera 8 than the iris 6. Consequently, the intensity of the scattered light will increase above the reference intensity at position A, as shown in FIG. 8. At position B, the light spot is completely focused onto the white sclera 8, which will result in an intensity signal that approaches the maximum intensity. As the light moves downward to position C, it is now almost completely covering the iris 6, which will result in a light intensity lower than the 50% reference value. Likewise, at position D, the light spot is completely focused onto the iris 6 which results in the minimum intensity signal as shown in FIG. 8.

The resulting signal will approximate a sinusoidal signal that contains the magnitude and phase of the eye displacement. This signal can be compared to the reference signal to determine both the phase and magnitude of the eye displacement. If the eye is being tracked during a surgical procedure, this information can be transmitted to the processor to modify the ablation algorithm to take into account the different positions of the eye relative to the optical axis of the laser and focusing optics. Thus, the laser beam can be modulated or otherwise modified so that the desired ablation shape on the eye is not effected by its relative movement.

Figure 9:
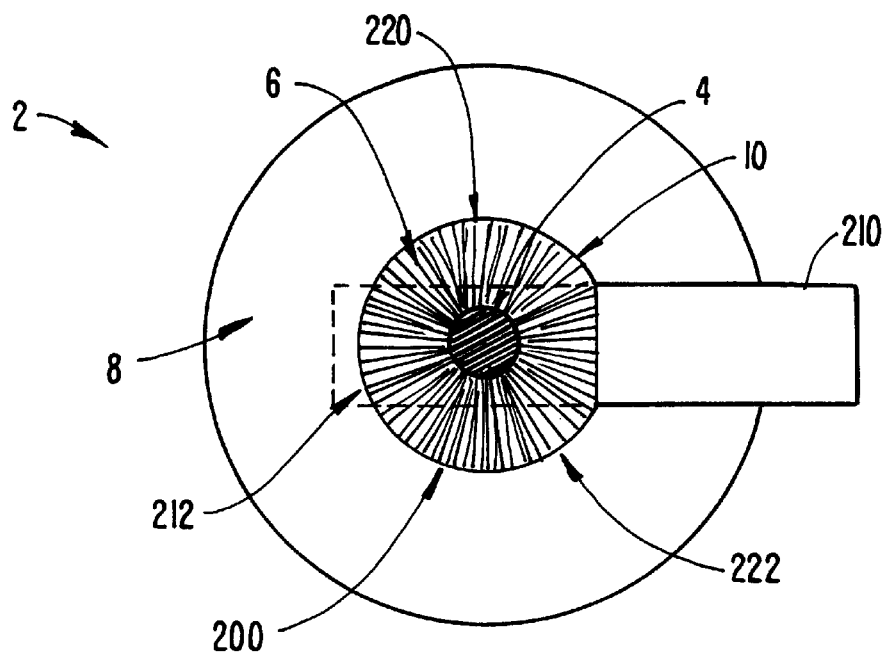
FIGS. 9 and 9A are schematic views of the light spot scanning around the iris/sclera boundary during a LASIK procedure.
Figure 9A:
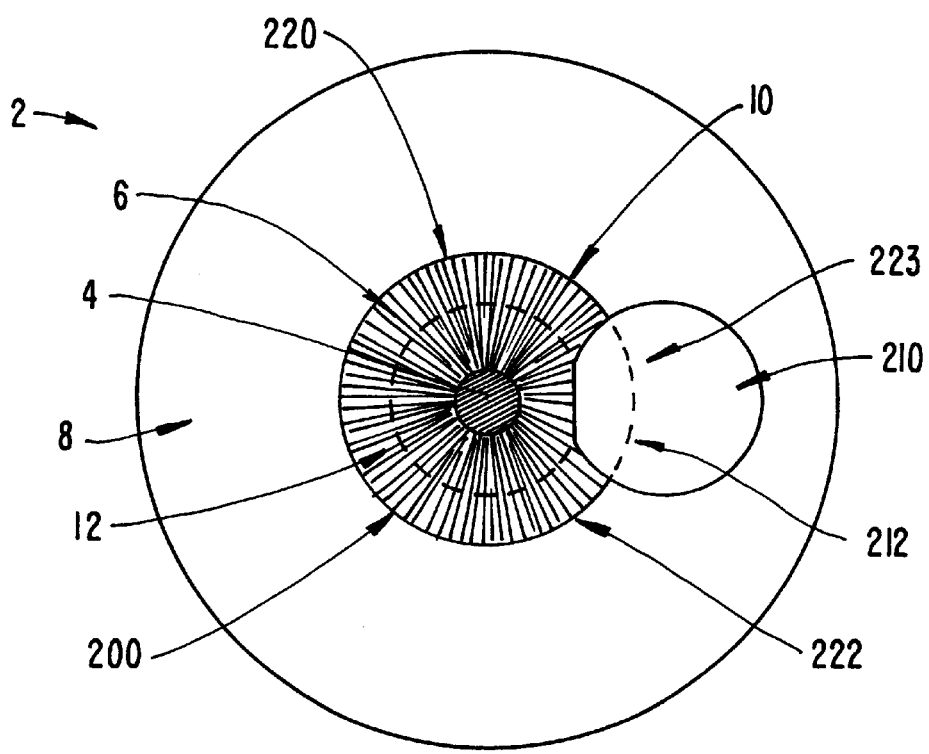

Referring to FIG. 9, a method for tracking the relative movement of the eye during a LASIK procedure will now be described. In LASIK procedures, the epithelium, and Bowman's membrane, and a portion of the anterior stroma are partially incised from the stroma and folded back (or completely removed) to expose the stroma to the laser. As shown in FIG. 9, this flap 210 is generally a rectangular piece of tissue that extends from the sclera 8 and one side of the iris 6 across the entire iris 6 and pupil 4 to the sclera 8 on the other side. Alternatively, the flap need not extend across the entire cornea, and the incision may be limited to a portion of the cornea as illustrated in FIG. 9A. Of course, it will be recognized that flap 210 may have a variety of shapes other than rectangular. For example, the flap may be circular as illustrated in FIG. 9A. The appearance of an underlying region 212 has been altered by the incision to present a poorly defined boundary. Accordingly, any light scattered from this region 212 will contain little meaningful value for determining the position of the eye.

As shown in FIG. 9, the present invention has the distinct advantage that the spinning trajectory 200 generally extends around the entire limbus 10 of the eye. The portions 220, 222 of trajectory 200 that extend below and above the removed flap 210 will be relatively unaffected by the incision. Accordingly, the information from these regions can be used to extrapolate the entire position of the limbus 10, including the portion that has now been incised or covered. Specifically, the spot trajectory 200 is calibrated prior to the LASIK procedure as discussed above. After the flap 210 has been incised, the light is scanned around the predetermined calibrated spot trajectory 200. The light passing through the upper and lower portions 220, 222 of the trajectory 200 will be processed as discussed above. Since the trajectory is a known shape (i.e., a circle, oval, etc) the entire trajectory can be interpolated from the information obtained from the upper and lower regions 220, 222.

Figure 10:
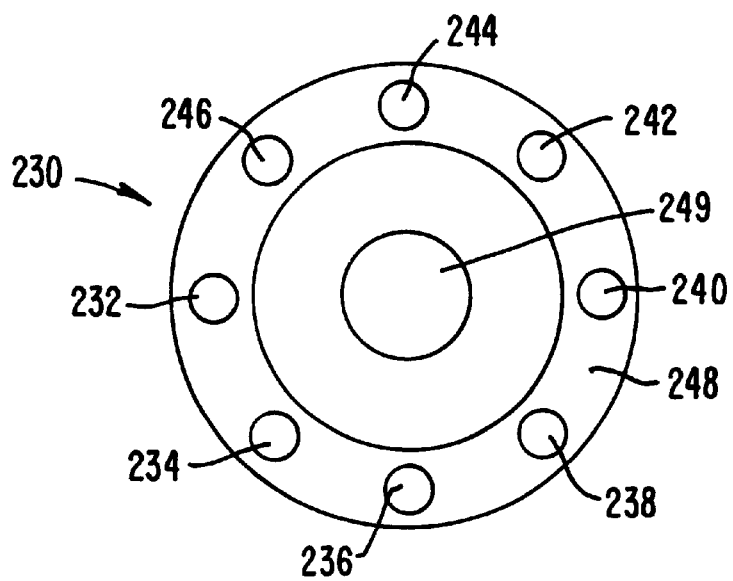
FIG. 10 is a schematic view of a ring of light sources for incorporating into an embodiment of the invention.

In an alternate embodiment, the light spot 202 may be scanned around trajectory 200 using a ring of light sources as shown in FIG. 10. A ring of light sources 230 includes a plurality of light sources 232, 234, 236, 238, 240, 242, 244 and 246 positioned so as to define an annular array 248. A light detector 249 is positioned to detect light reflected from eye 2. The ring 230 is positioned so that an individual light source such as 232 produces a projected light spot 202 on eye 2. The sequential activation of light sources 232 to 246 causes the projected light spot 202 to scan around trajectory 200. The light reflected from projected spot 202 is converted to corneal margin signal 122 by light detector 249.

Figure 11:
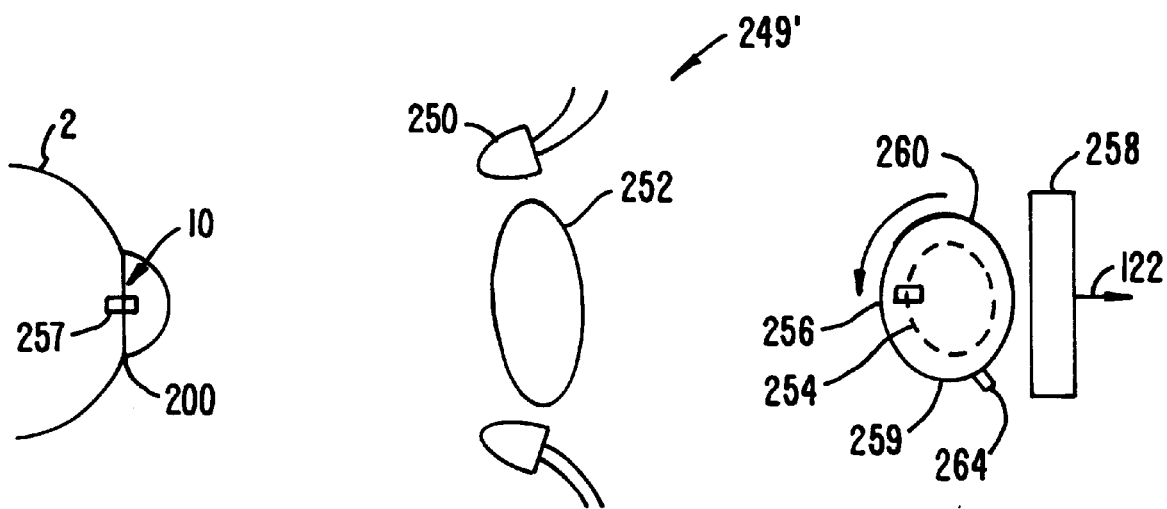
FIG. 11 schematically illustrates the use of a rotating aperture in an embodiment of the invention.

As illustrated in FIG. 11, the measured region of the limbus may be scanned using a uniform illumination source and selective light detection. An optical train 249' here includes an imaging lens 252 and a rotating disc 260. A limbus 10 of eye 2 is illuminated with a light energy source 250 directing light energy at the eye and so as to provide nearly uniform illumination of the limbus 10. An imaging lens 252 forms an image 254 of eye 2 near the surface of an optically non-transmitting material 259, here in the form of a rotating disc 260. The image 254 of eye 2 includes the limbus 10. The trajectory 200 of the measured region 257 is positioned to be coincident with the limbus 10. The disc 260 includes an aperture 256 formed in the optically non-transmitting material 259. The aperture 256 is positioned in front of a detector 258.

The detector 258 generates an electrical signal for measuring an intensity of the light energy reflected from the eye. A dimension across the measured region 257 of the eye 2 is restricted to the portion of image 254 that selectively passes through the aperture 256 formed in the rotating disc 260. The disc 260 excludes the light rays outside the measured region 257 from reaching the detector 258. Rotating disc 260 will cause the aperture 256 to rotate about the image 254 of the limbus 10 that is formed on disc 260. This rotation of the aperture 256 about the image 254 will cause the measured region 257 of eye 2 to scan around a trajectory 200.

In some embodiments, the aperture 256 may be movably supported on a guide (not shown) that slides radially along the disc 260 to adjust the radius of the trajectory 200 of the measured region 257. This adjustment is preferably performed to match the radius of rotation of the aperture 256 with the radius of the image 254 of limbus 10. This adjustment causes the radius of the trajectory 200 of the measured region 257 to match the radius of the limbus 10.

Rotating aperture 256 around the image 254 of limbus 10 produces a varying corneal margin signal 122 from light detector 258. The position of the eye is determined from a variation in the intensity of the reflected light energy. The rotation of disc 260 may be synchronized with the measurement of electrical signal 262 by rotating synchronization flag 264 across a sensor to produce a reference signal 119.

Figure 12:
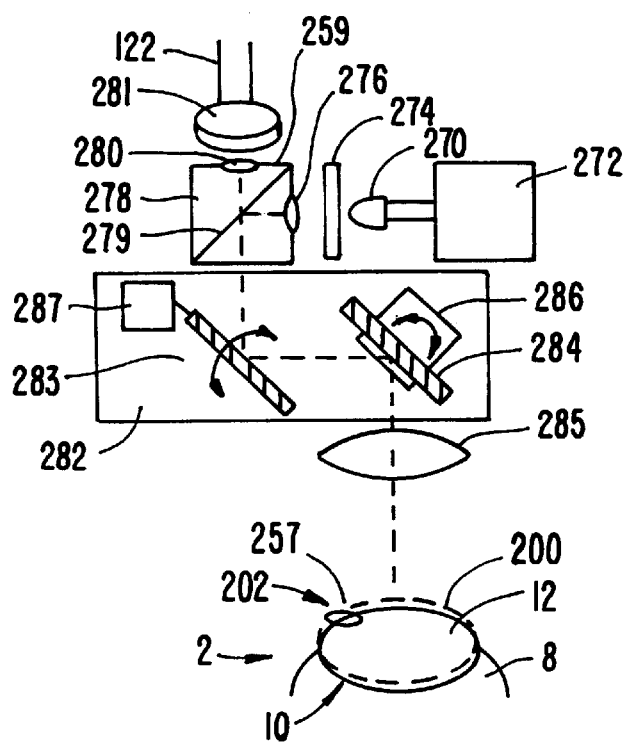
FIG. 12 schematically illustrates an embodiment of the invention using a projected spot aligned with an aperture to scan a measured region around the limbus.

In another alternate embodiment of the invention, the measured region is scanned by moving optical elements as illustrated in FIG. 12. A light source 270 emits a visible light energy that is reflected from the measured region 257 of an eye 2. The light source 270 is preferably driven by a pulsed light source driver 272 to produce light pulses at a desired fixed frequency. Although less preferred, a light chopper may be positioned in the path of light from light source 270 to produce pulsed light at a desired frequency.

A polarizer 274 may be positioned between the light source 270 and an aperture 276. The polarizer 274 passes polarized light to the aperture 276. The aperture 276 selectively passes the polarized light. The polarized light illuminates a polarizing beam splitter 278. The polarizing beam splitter 278 has a reflecting surface 279 that reflects the polarized light toward the eye 2. The polarized light that is reflected by the measured region of eye 2 is generally not completely polarized when it returns to polarizing beam splitter 270. Therefore, a portion of the reflected light from the region will pass through polarizing beam splitter 278.

A plate comprising an optically non-transmitting material 259 is positioned in the path of the light passed by beam splitter 278. An aperture 280 is formed in the optically non-transmitting material 259 and restricts a dimension across the measured region 257 by selectively passing the light to a detector 281 and the optically non-transmitting plate excludes light outside the measured region from passing to the detector. The light detector 281 converts the light into electrical corneal margin signal 122.

An imaging lens 285 is positioned along the optical path between the two apertures and the eye. The imaging lens 285 projects an image of aperture 276 on the eye 2 so as to form a focused beam of visible light energy that intersects the eye to form a visible light spot 202. The imaging lens also forms an image of the measured region 257 on the aperture 280. The projected light spot 202 is aligned so as to pass through aperture 280 after being reflected from the surface of eye 2. The reflecting surface 279 of the polarizing beam splitter 278 aligns the projected light spot 202 with the measured region 257 so that the projected light spot 202 and the measured region 257 are confocal on the eye 2. This confocal arrangement of the two apertures desirably improves the signal to noise ratio of the measured signal and is especially effective in suppressing optical noise from lights present under an operating microscope.

The measured region 257 may be scanned around the trajectory 200 with light beam deflection module 282. The light beam deflection module scans both the projected spot 202 and the region of the eye selected by detector aperture 280. By rotating the light spot 202 and the measured region 257 around the eye at a reference frequency in a pattern comprising the annular trajectory 200, a varying corneal margin signal 122 is generated at the reference frequency. The light beam deflection module 282 comprises movable mirrors 283 and 284. Alternatively, other moving optical elements besides mirrors such as lenses and prisms may be used. The mirrors 283 and 284 are mechanically coupled to galvanometers 286 and 287. Although galvanometers are used in this embodiment, any suitable drives such as stepper motors, servo motors and piezo electric transducers may also be employed. By suitably rotating mirrors 283 and 284, measured region 257 and light spot 202 are scanned around trajectory 200.

Figure 13:
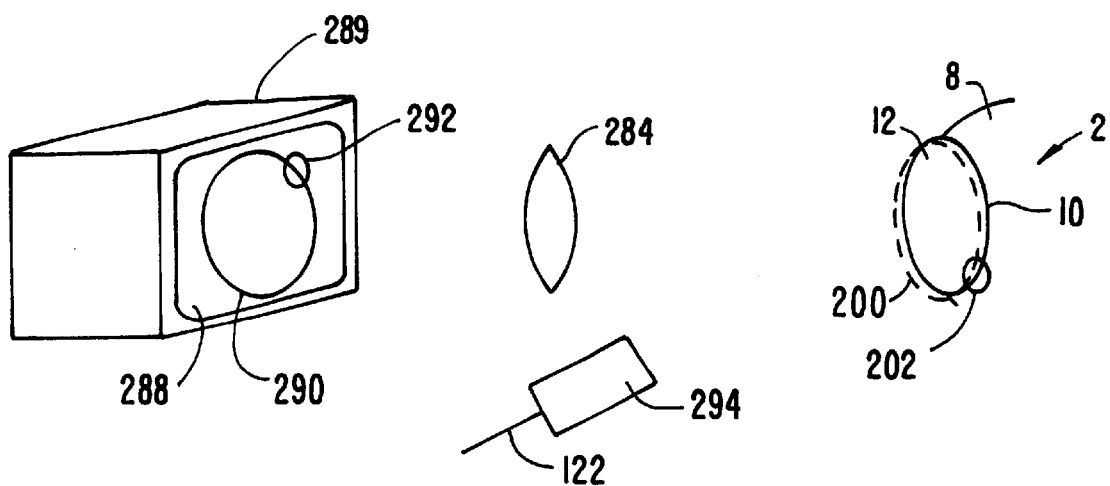
FIG. 13 schematically illustrates an embodiment of the invention that includes a cathode ray tube screen to project a visible light spot onto the eye.

In yet another alternate embodiment of the invention, the visible light spot 202 is scanned by projecting a light spot comprising a beam of visible light energy from a video display onto the eye as illustrated in FIG. 13. A cathode ray tube 289 comprises a screen 288 on which a light spot 292 appears. The light spot 292 travels around a trajectory 290 on the cathode ray tube screen. Although a cathode ray tube is illustrated, any suitable display such as a super luminescent display, liquid crystal display or active matrix display may also be used. A lens 284 projects an image of light spot 292 onto the eye 2 so as to form light spot 202. The light spot 202 travels around a trajectory 200. A light detector 294 is positioned to receive light reflected by eye 2. The reflected light is converted to electrical corneal margin signal 122 by the detector 294.

Figure 14:
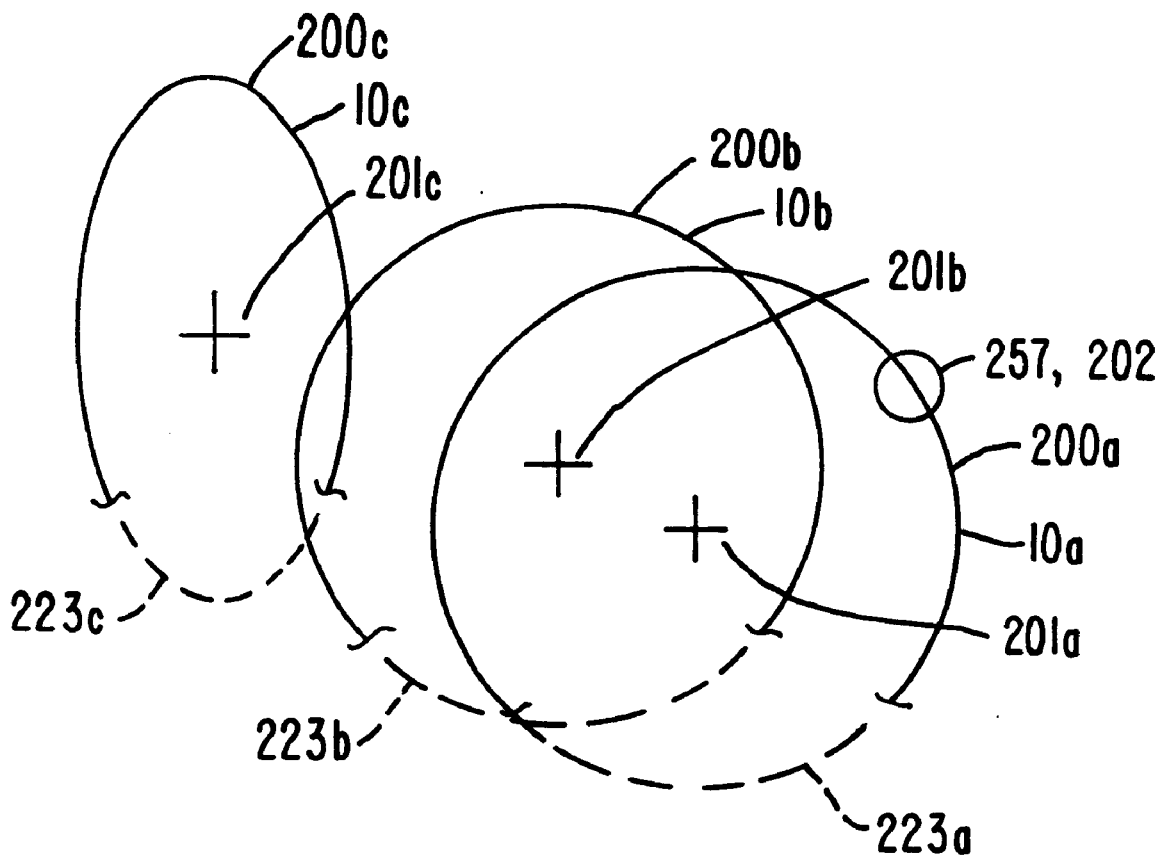
FIG. 14 schematically illustrates an embodiment of the invention that includes blanking the projected light spot over a covered region of the limbus and displacing the trajectory of the scanning light spot to match the position of the eye.

In another embodiment of the invention, the eye tracker further provides for automatically detecting the presence of a LASIK flap, for pulsing and blanking the projection of a visible light spot, and for displacing the trajectory 200 so that the position of the trajectory corresponds to the position of the eye as illustrated in FIG. 14. A measured region 257 scans around a trajectory 200. The measured region 257 comprises a light spot 202. Preferably, the light spot 202 is formed as illustrated above by projecting a light spot from a video screen onto an eye 2. Alternatively, other techniques as illustrated above may be used to scan the measured region. For example, a projected light spot that is confocal with a measured region may be utilized.

A first trajectory 200*a* is substantially aligned with the limbus 10*a*. During a blanked portion 223 of the scan around the trajectory 200*a*, the light source is turned off and the data are interpolated. During LASIK, this blanked portion will correspond to the underlying region 212. As the eye moves, a signal is generated which indicates the direction and magnitude of the eye movement as illustrated above. The trajectory is displaced in the direction of the eye motion resulting in a displaced trajectory 200*b*. Further movement of the eye will result in a further displacement of the trajectory. If desired, the scanned trajectory may be an oval or other shape such as 200*c*. This oval shape may be desirable in situations where the eye moves so as to appear elliptical.

Figure 15:
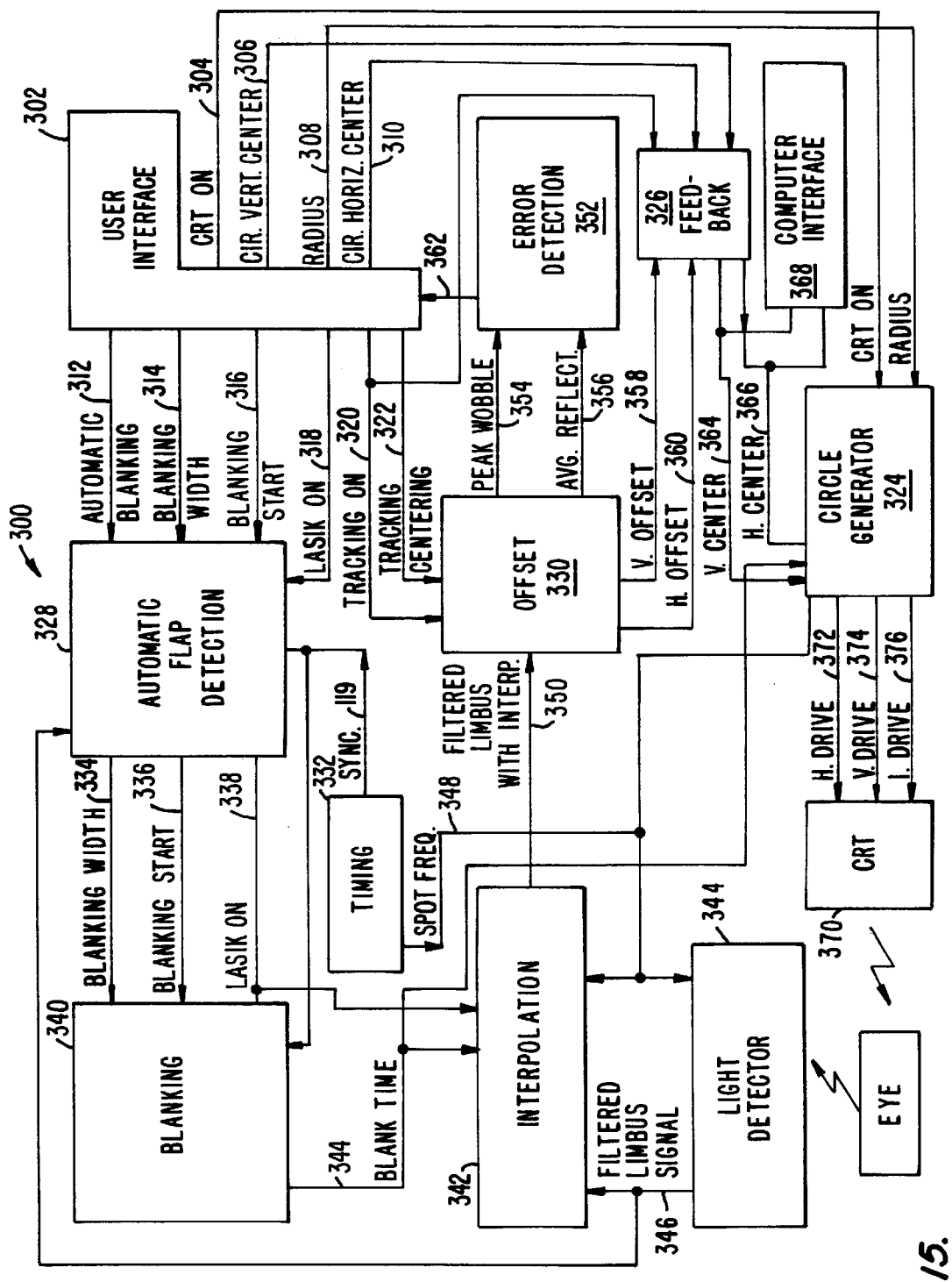
FIG. 15 is a block diagram that schematically illustrates a control circuit that provides for displacing and blanking the scanning light spot as in FIG. 14.

A control circuit 300 for controlling the eye tracker and the position of the trajectory 200 is schematically illustrated in FIG. 15. This circuit will now be discussed in detail. The control circuit 300 includes a user interface circuit 302, an automatic flap detection circuit 328, a blanking circuit 340, an interpolation circuit 342, an offset circuit 330, an error detection circuit 352, a light detector circuit 344, a feedback circuit 326, a computer interface circuit 368, a circle generator 324 and a CRT circuit 370. Once again, those of skill in the art should recognize that the invention is not inherently limited to the specific arrangement of analog and digital electrical circuits shown. For example, in some embodiments, digital data processing hardware/software systems may replace (substantially directly, or with modifications) at least some of the analog functions and components of these circuits.

The user interface 302 makes use of a CRT on signal 304 electrically coupled to a circle generator 324. A circle vertical center signal 306 and a circle horizontal center 310 are electrically coupled to a feedback circuit 326. A radius signal 308 is electrically coupled to a circle generator 324. An automatic blanking signal 312, a blanking width signal 314, a blanking start signal 316 and a LASIK on signal 318 are electrically coupled to automatic flap detection circuit 328. A tracking on signal 320 and a tracking centering circuit 322 are coupled to an offset circuit 330. The tracking on signal 320 is also electrically coupled to feedback circuit 326.

The automatic flap detection circuit 328 is electronically coupled to a blanking circuit 340, a timing circuit 332, the detector circuit 344 and an interpolation circuit 342. A reference synchronization signal 119 is electrically coupled to the timing circuit 332. A blanking width signal 334, a blanking start signal 336 and a LASIK on signal 338 are electrically coupled to blanking circuit 340. The LASIK on signal 338 is also electrically coupled to interpolation circuit 342. A filtered limbus signal 346 of detector circuit 344 is electrically coupled to automatic flap detection circuit 328.

The blanking circuit 340 is electrically coupled to the timing circuit 332 and the interpolation circuit 342. The reference synchronization signal 119 from the timing circuit 332 is input into the blanking circuit 340. The blank time signal 344 is electrically coupled to the interpolation circuit 342.

The interpolation circuit 342 is electrically coupled to the detector circuit 344, the timing circuit 332 and the offset circuit 330. The filtered limbus signal 346 from the detector 344 is coupled to the interpolation circuit 342. The spot frequency signal 348 from the timing circuit 332 is coupled to the interpolation circuit 342 and the detector circuit 344. The filtered limbus signal with interpolation 350 from the interpolation circuit 342 is coupled to the offset circuit 330.

The offset circuit 330 is electrically coupled to the interpolation circuit 342, the user interface circuit 302, the error detection circuit 352 and the feedback circuit 326. The peak wobble 354 and average limbus signal 356 are electrically coupled to error detection circuit 352. The vertical offset signal 358 and horizontal offset signal 360 are electrically coupled to the feedback circuit 326.

The error detection circuit 352 is electrically coupled to the user interface 302 and offset circuit 330. An error signal 362 is coupled to user interface 302.

The feedback circuit 326 is electrically coupled to the user interface circuit 302, the offset circuit 330, the circle generator circuit 324 and the computer interface circuit 368. The vertical center signal 364 of feedback circuit 326 is electrically coupled to the circle generator 324 and computer interface 368. The horizontal center 366 is electrically coupled to the circle generator 324 and computer interface 368.

The circle generator 324 is electrically coupled to the cathode ray tube 370, the feedback circuit 326, and the user interface 302. The horizontal drive 372, the vertical drive 374 and the intensity drive 376 are electrically coupled to the CRT 370.

Figure 15A:
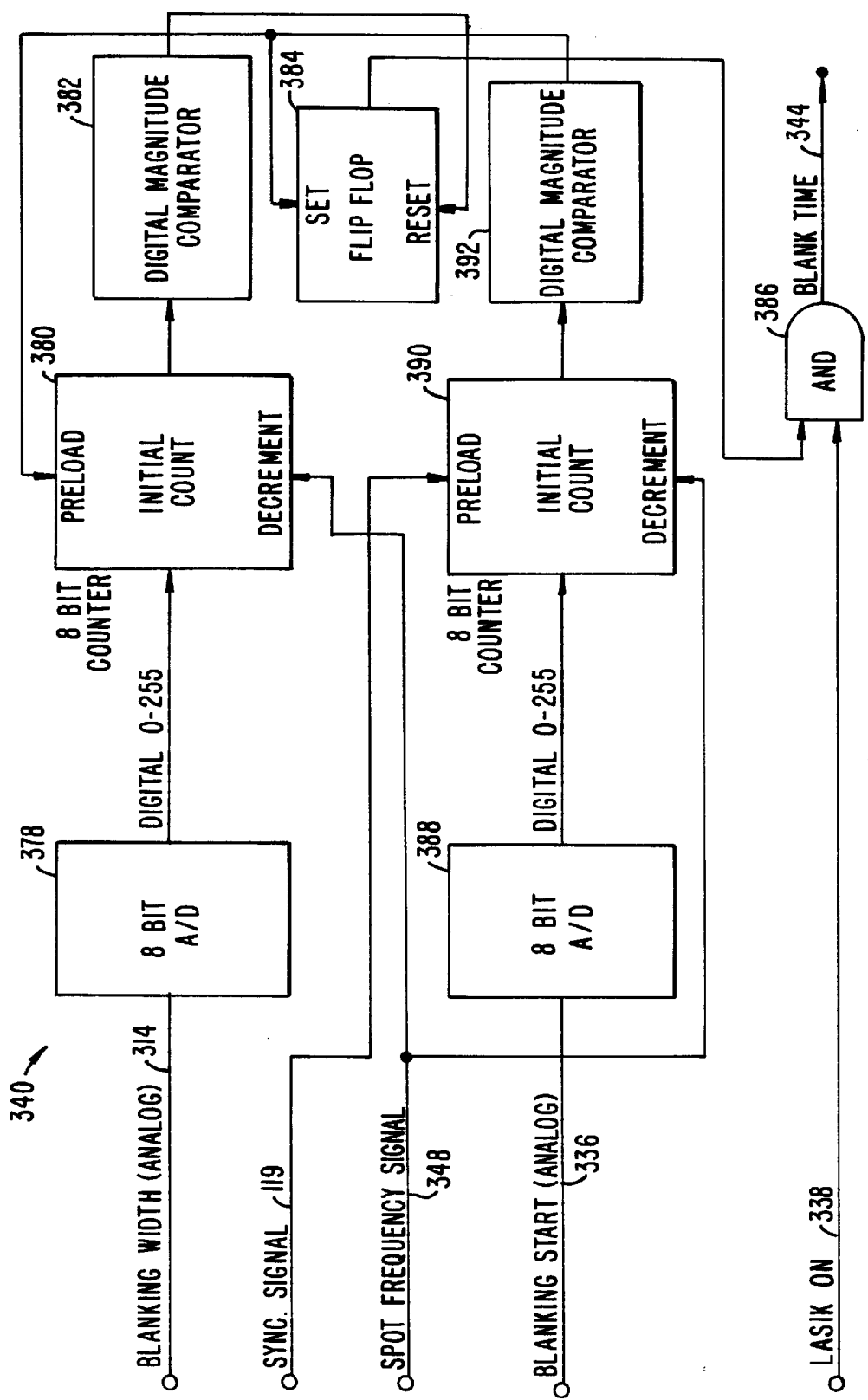
FIG. 15A is a block diagram illustrating a blanking circuit referred to in FIG. 15.

The blanking circuit 340 is schematically illustrated in FIG. 15*a*. This circuit generates a signal blank time 344 that is used to synchronize the interpolation of the measured intensity with the turning off of the projected light spot 202. The blanking width signal 314 is input in to a 8 bit analog to digital converter 378. The digital output of the analog to digital converter 378 is input as the initial count of an 8 bit counter 380. The spot frequency signal 348 is input to the 8 bit counter 380. The output of the 8 bit counter 380 is input to a digital magnitude comparator 382. The output of the digital magnitude comparator 382 is input to the reset of a flip/flop 384. The blanking start signal 336 is input to an 8 bit analog to digital converter 388. The digital output of the analog to digital converter 388 is input as an initial count to an 8 bit counter 390. The reference synchronization signal 119 is input to preload of the 8 bit counter 390. The spot frequency signal 348 is input to decrement the 8 bit counter 390. The output of the 8 bit counter 390 is input to the digital magnitude comparator 392. The output of the comparator 392 is input to set flip/flop 384 and pre-load counter 380. The output of flip/flop 384 is input to AND gate 386. The LASIK on signal 338 is input to AND gate 386. The output of AND gate 386 is blank time 344.

Figure 15B:
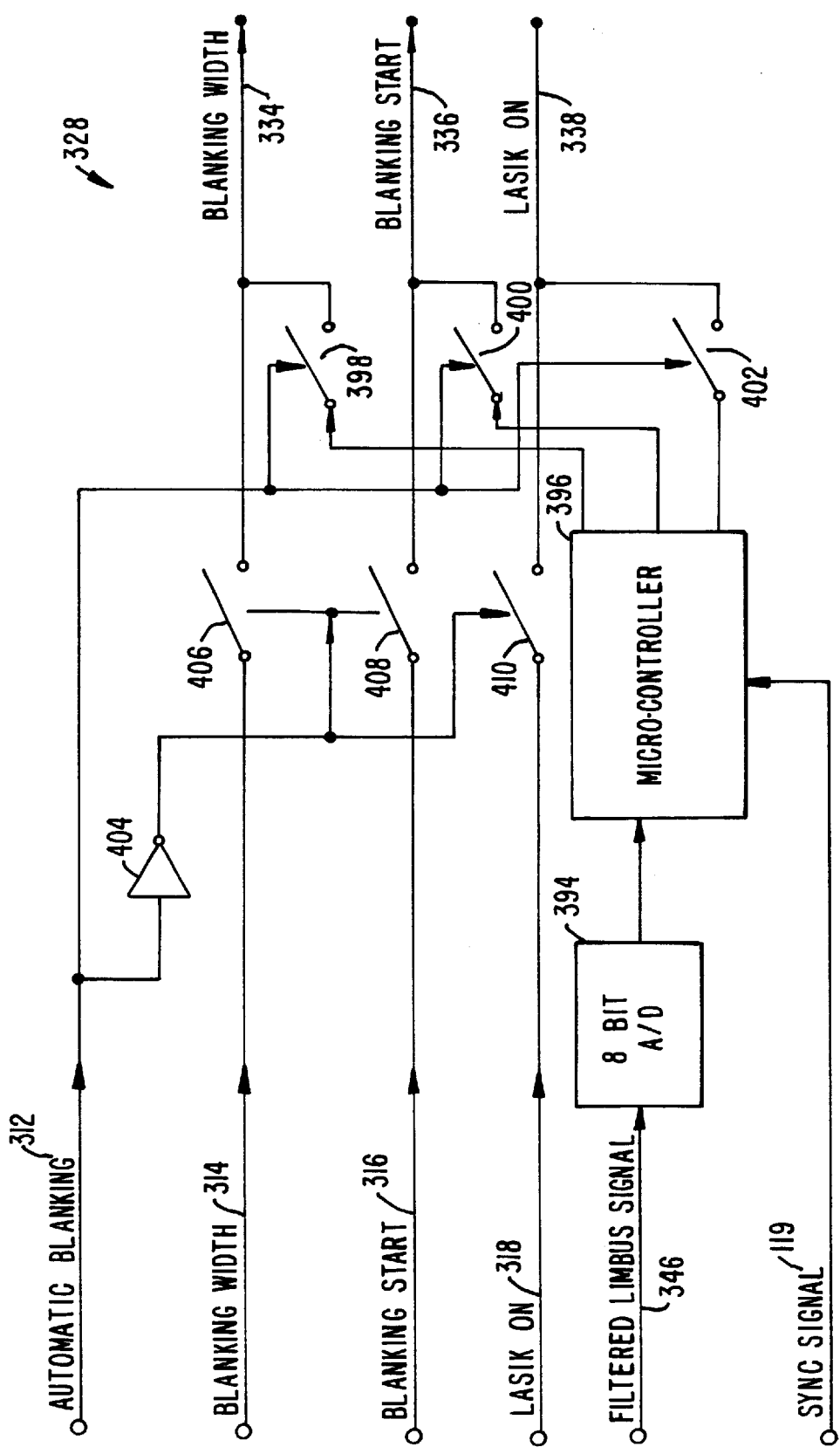
FIG. 15B is a block diagram illustrating an automatic flap detection circuit referred to in FIG. 15.

The automatic flap detection circuit 328 is schematically illustrated in FIG. 15B. This circuit is used to automatically detect the presence of an object covering the limbus such as an eyelid or LASIK flap. This circuit automatically adjusts the interpolation and scanning of the projected spot. The presence of the flap may be detected by an abrupt change in the measured signal intensity when the projected spot passes over the edge of the flap. The filtered limbus signal 346 is input to an 8 bit analog to digital converter 394. The digital output of the analog to digital converter 394 is input to a microcontroller 396. The reference synchronization signal 119 is input to the microcontroller 396. The automatic blanking signal 312 is input to switches 398, 400 and 402. A NOT gate 404 inputs the opposite of blanking signal 312 to switches 406, 408 and 410. When automatic blanking signal 312 is true, switches 406, 408 and 410 are open, and switches 398, 400 and 402 are closed to output the blanking width 334, blanking start 336 and LASIK on 318 signals from microcontroller 396.

Figure 15C:
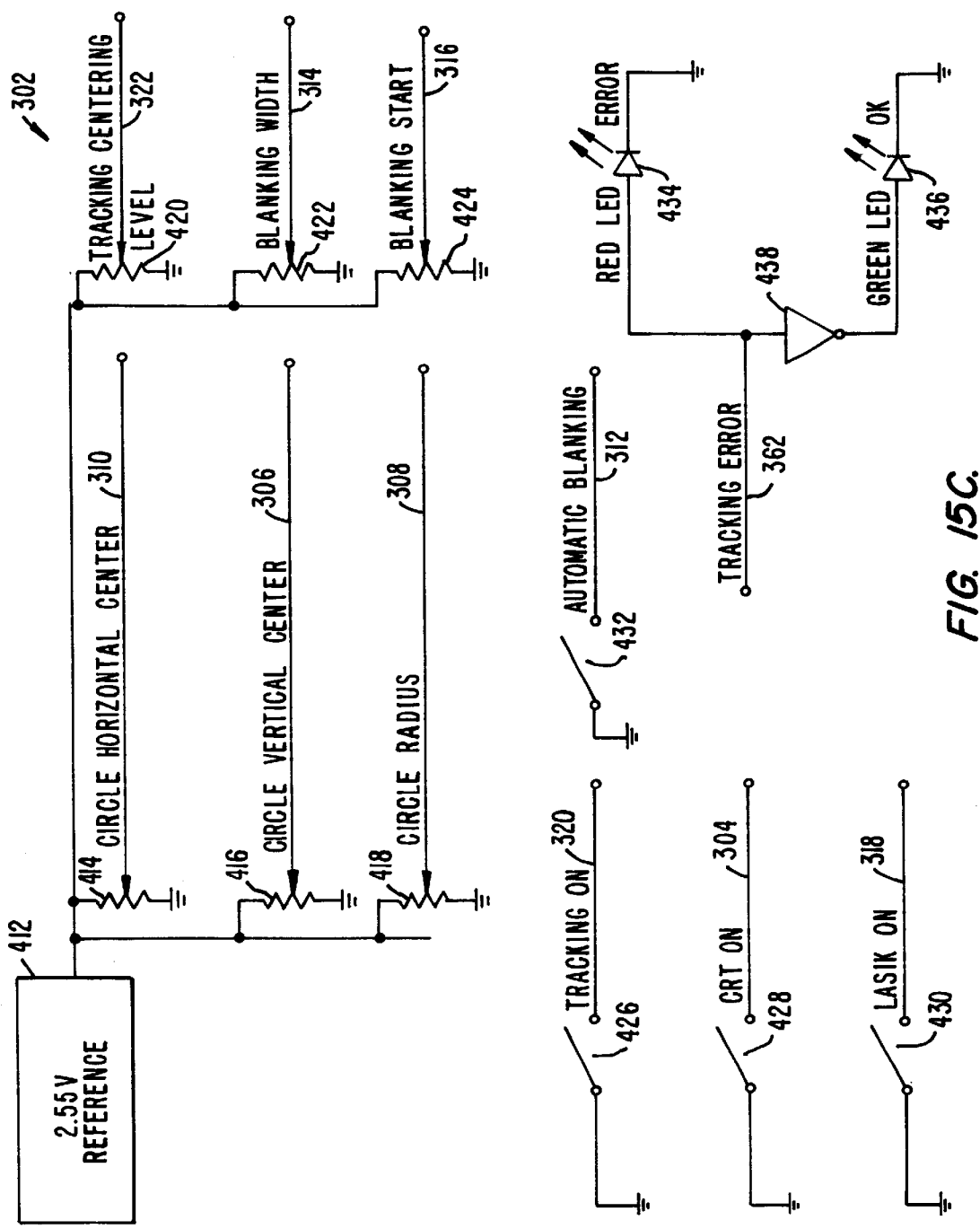
FIG. 15C is a block diagram illustrating a user interface circuit referred to in FIG. 15.

The user interface circuit 302 is schematically illustrated in FIG. 15c. A reference voltage 412 is applied across a variable resistors 414 to 424. The variable resistors 414 to 424 are adjusted to produce desired voltages for the circle horizontal center 310, the circle vertical center 306, the circle radius 308, the tracking centering level 322, the blanking width 314 and the blanking start 316 respectively. The tracking on signal 320 is activated by a switch 426. The CRT on signal is activated by closing a switch 428. The LASIK on signal 318 is activated by closing a switch 430, and the automatic blanking signal 312 is activated by closing a switch 432. A tracking error signal 434 is used to activate a red LED 434 to indicate a tracking error. The tracking error signal 362 is also input to a NOT gate to activate a green LED to indicate tracking when the error signal 362 is not active.

Figure 15D:
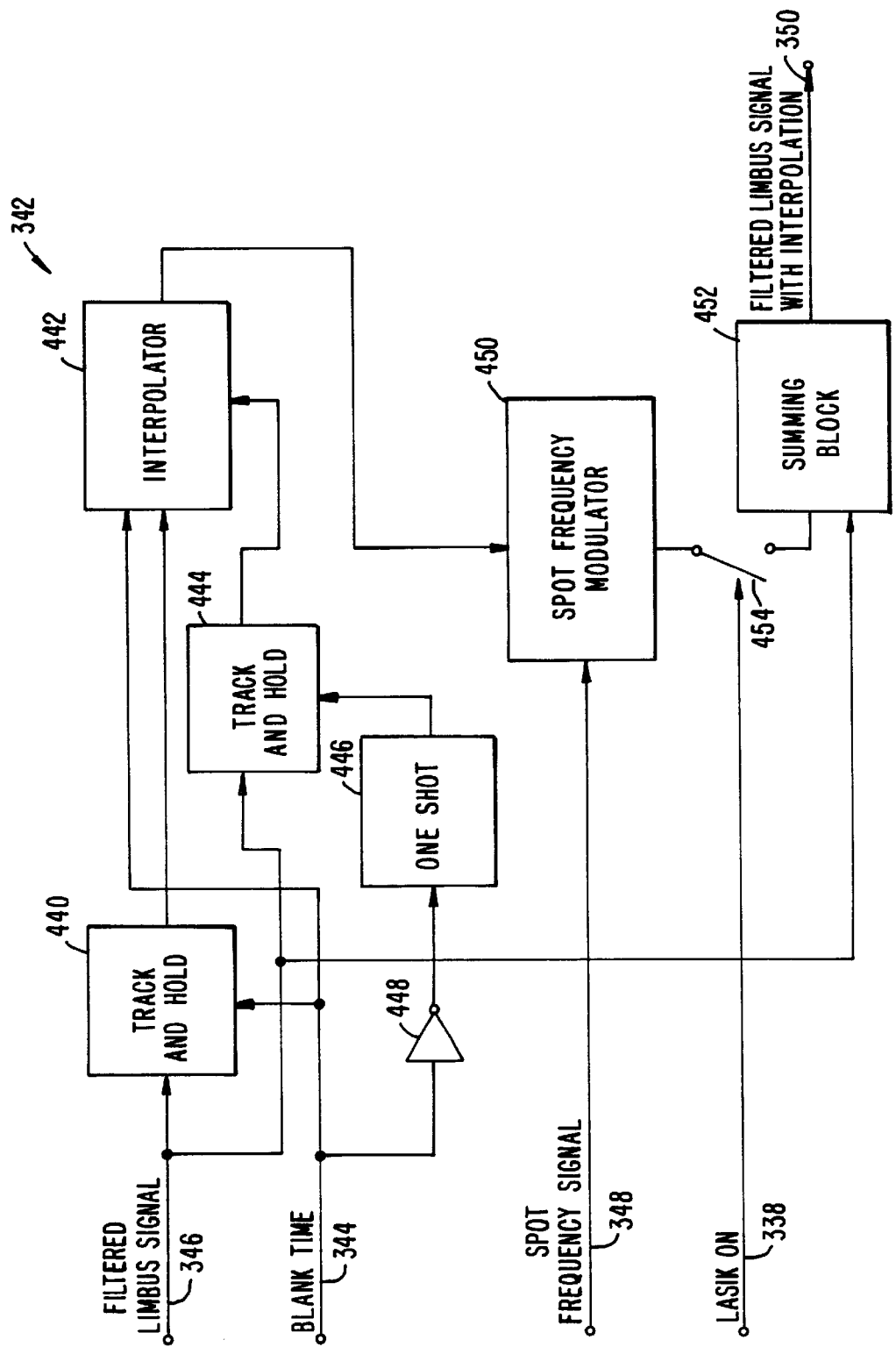
FIG. 15D is a block diagram illustrating an interpolation circuit referred to in FIG. 15.

The interpolation circuit 342 is schematically illustrated in FIG. 15d. The filtered limbus signal 346 is input to a track and hold 440. The blank time signal 344 is also input to the track and hold 440. The output of the track and hold 440 is input to the interpolator 442. The filtered limbus signal 346 is input to track and hold 444. A NOT gate 448 receives the blank time signal 344 and outputs a voltage to an input of the one shot 446. The one shot 446 outputs a voltage to the track and hold 444. The track and hold 444 is input to interpolator 442. The track and hold 440 and the track and hold 444 input the endpoint voltages to be interpolated between by interpolator 442. The interpolator 442 uses the input voltages from the track and holds 440 and 444 to interpolate the signal between the two endpoint voltages. The interpolator 442 may be constructed from a combination of analog and digital electronics. Alternatively, the interpolator may be constructed from a microcontroller. The interpolator 442 also receives as input the blank time signal 344. The spot frequency signal 348 is input to a spot frequency modulator 450. The interpolator 442 outputs an interpolated voltage to the spot frequency modulator 450. When the LASIK on signal 338 is active, the output of spot frequency modulator 450 becomes input to summing block 452 by the closing of switch 454. The filtered limbus signal 346 is also input to the summing block 452. The output of the summing block 452 is the filtered limbus signal with interpolation 350.

Figure 15E:
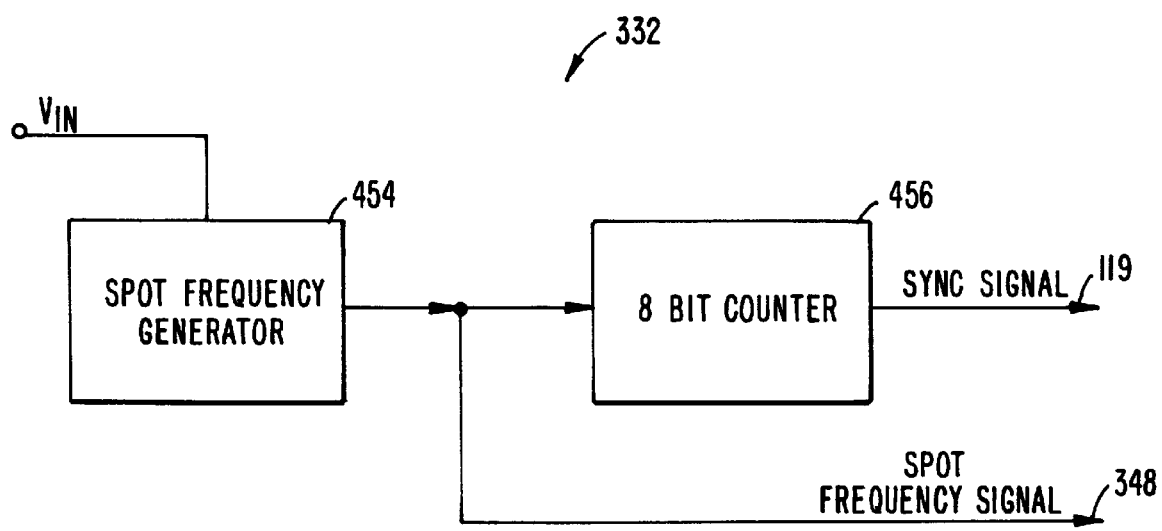
FIG. 15E is a block diagram illustrating a timing circuit referred to in FIG. 15.

The timing circuit 332 is schematically illustrated in FIG. 15e. A voltage is applied to a spot frequency generator 454. The spot frequency generator is preferably a crystal oscillator, but could be any suitable oscillator readily constructed by a person skilled in the art of electronics. The spot frequency generator generates the spot frequency signal 348. The spot frequency signal 348 is input to an 8 bit counter 456. The output of the 8 bit counter 456 generates the synchronization reference signal 119 every 256 oscillations of spot frequency generator 454. Therefore, there are 256 pulses of light spot 202 for every rotation of the scanning region 257.

Figure 15F:
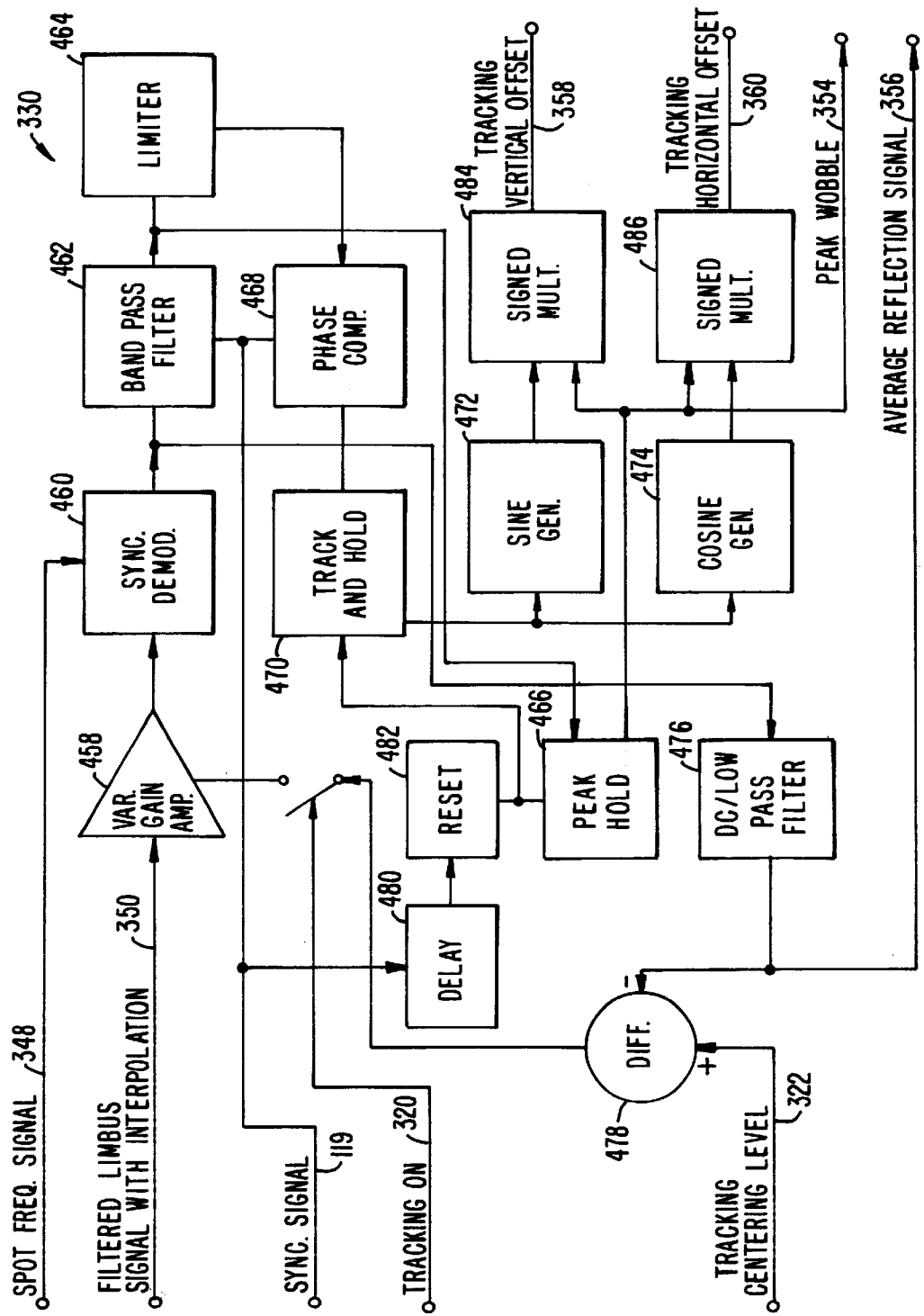
FIG. 15F is a block diagram illustrating an offset circuit referred to in FIG. 15.

The offset circuit 330 determines the offset of the limbus 10 relative to the trajectory 200 as illustrated in FIG. 15f. The filtered limbus signal with interpolation 350 is input to a variable gain amplifier 458. The output of the variable gain amplifier 458 is input to a synchronous demodulator 460. The output of the synchronous demodulator 460 is input to a tunable bandpass filter 462. The tunable bandpass filter is tuned to the spinning frequency by input of the reference synchronization signal 119. The output of tunable bandpass filter 462 is input to a limiter 464 and a peak hold 466. The output of limiter 464 is input to a phase comparator 468. The synchronization signal 119 is input to the phase comparator 468. The output of the phase comparator 468 is input to a track and hold 470. The output of the track and hold 470 is input to a sine generator 472 and a cosine generator 474. The output of the synchronous demodulator 460 is input to a DC/low pass filter 476. The output of the DC/low pass filter 476 is the average reflection signal 356. The average reflection signal 356 is input to a differential amplifier 478. The tracking centering level 322 is also input to the differential amplifier 478. The output of differential amplifier 478 is input to the variable gain amplifier 458. The synchronization signal 119 is input to a delay 480. The output of a delay 480 is input to a reset 482. The output of the reset 482 is input to a reset of the peak hold 466 and a reset of the track and hold 470. The output of the peak hold 466 is the peak wobble signal 354. The peak wobble signal 354 is input to the signed multipliers 484 and 486. The outputs of the signed multipliers 484 and 486 are the tracking vertical and horizontal offsets 358 and 360 respectively.

Figure 15G:
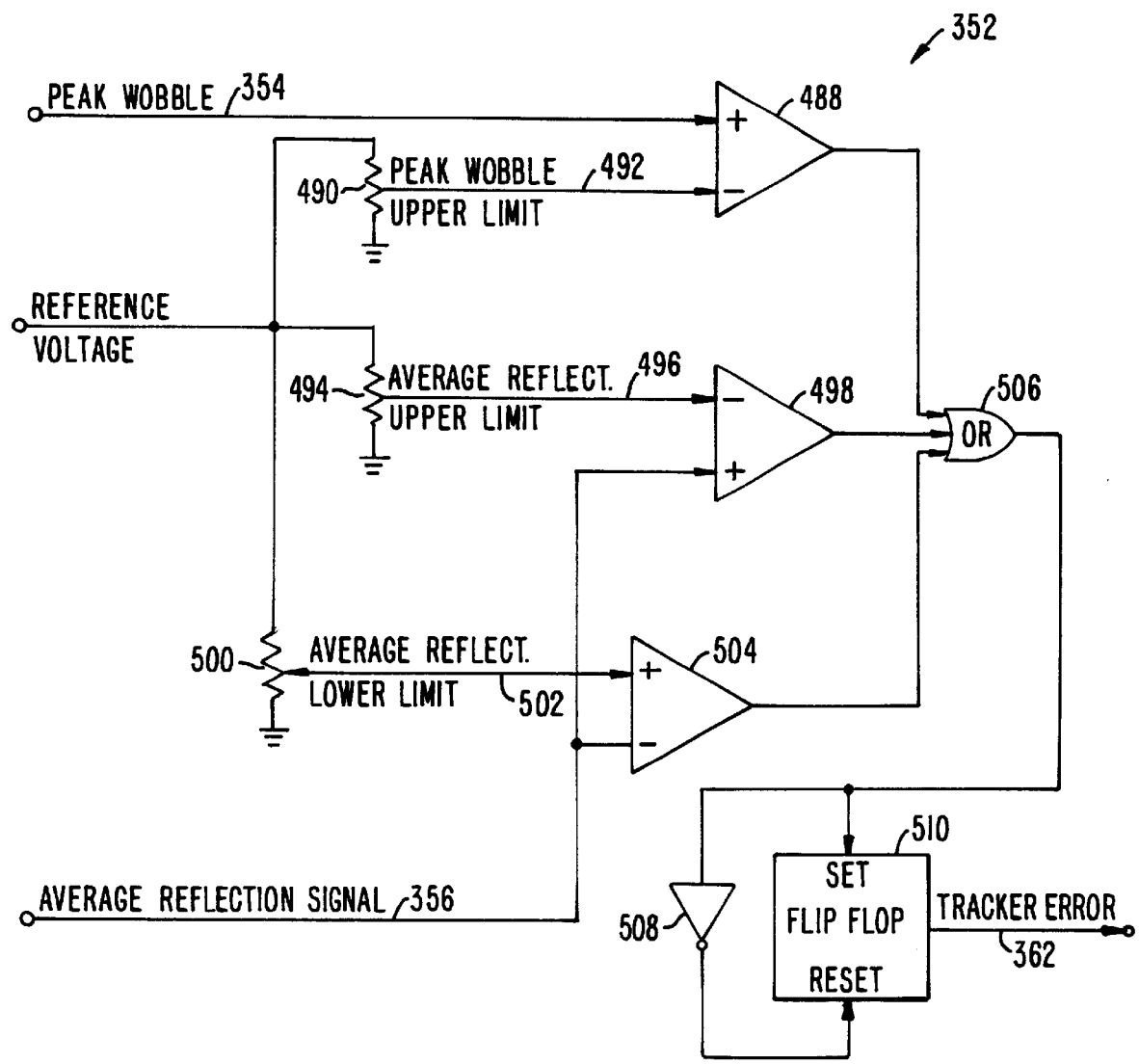
FIG. 15G is a block diagram illustrating an error detection circuit referred to in FIG. 15.

The error detection circuit 352 is schematically illustrated in FIG. 15g. This circuit detects tracking errors. The peak wobble signal 354 is input to a comparator 488. A variable resistor 490 sets the voltage for the peak wobble upper limit 492 that is also input to the comparator 488. The average reflection signal 356 is input to a comparator 498. A variable resistor 494 is used to set the average reflection upper limit voltage 496 that is input to the comparator 498. A variable resistor 500 is used to set the average reflection lower limit 502 that is input to a comparator 504. The output of the comparators 488, 498 and 504 are input to an OR gate 506. The output of the OR gate 506 is input to a NOT gate 508 and a set pin of a flip/flop 510. The output of the NOT gate 508 is input to a reset pin of the flip/flop 510. The output of the flip/flop 510 is the tracker error signal 362.

Figure 15H:
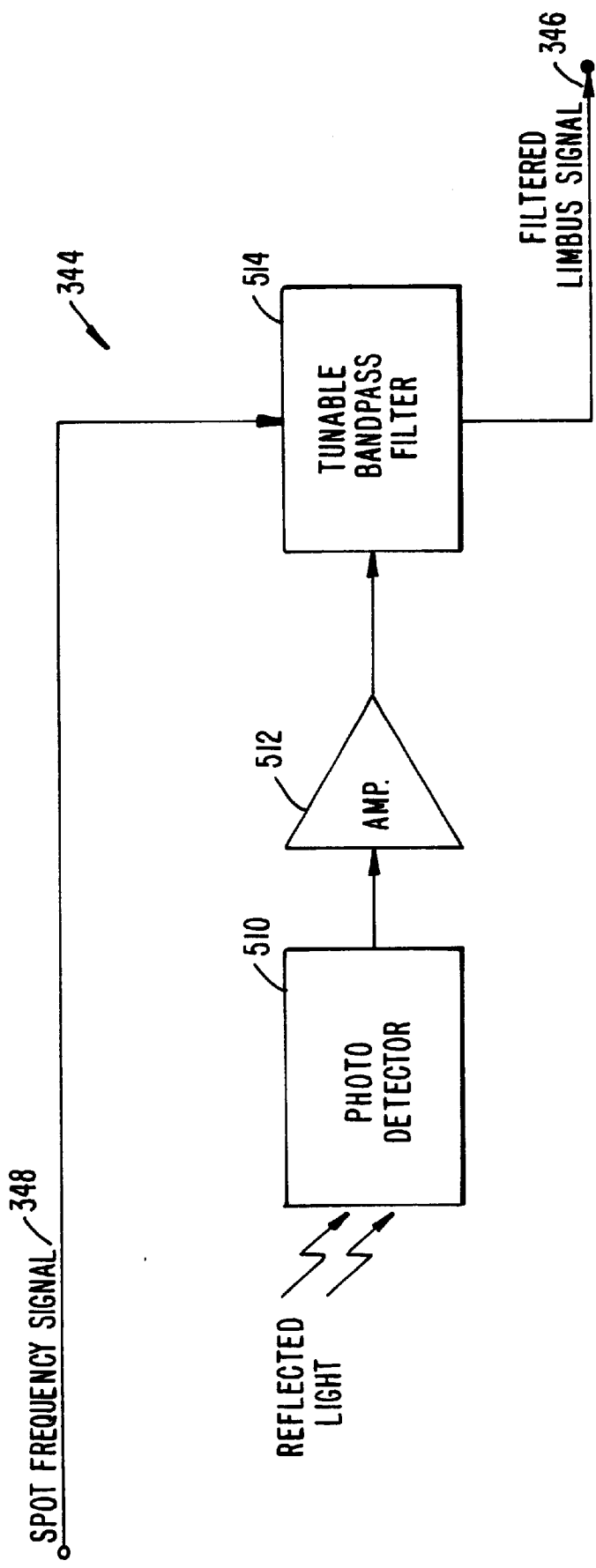
FIG. 15H is a block diagram illustrating a light detector circuit referred to in FIG. 15.

The light detector circuit 344 is schematically illustrated in FIG. 15h. Reflected light is converted to an electrical signal by a photo detector 510. The output of photo detector 510 is input to an amplifier 512. The output of amplifier 512 is input to a tunable bandpass filter 514. The spot frequency signal 348 is input to the tunable bandpass filter 514. The spot frequency signal 348 selectively tunes the bandpass filter 514 to the spot frequency. The output of the tunable bandpass filter 514 is filtered limbus signal 346.

Figure 15I:
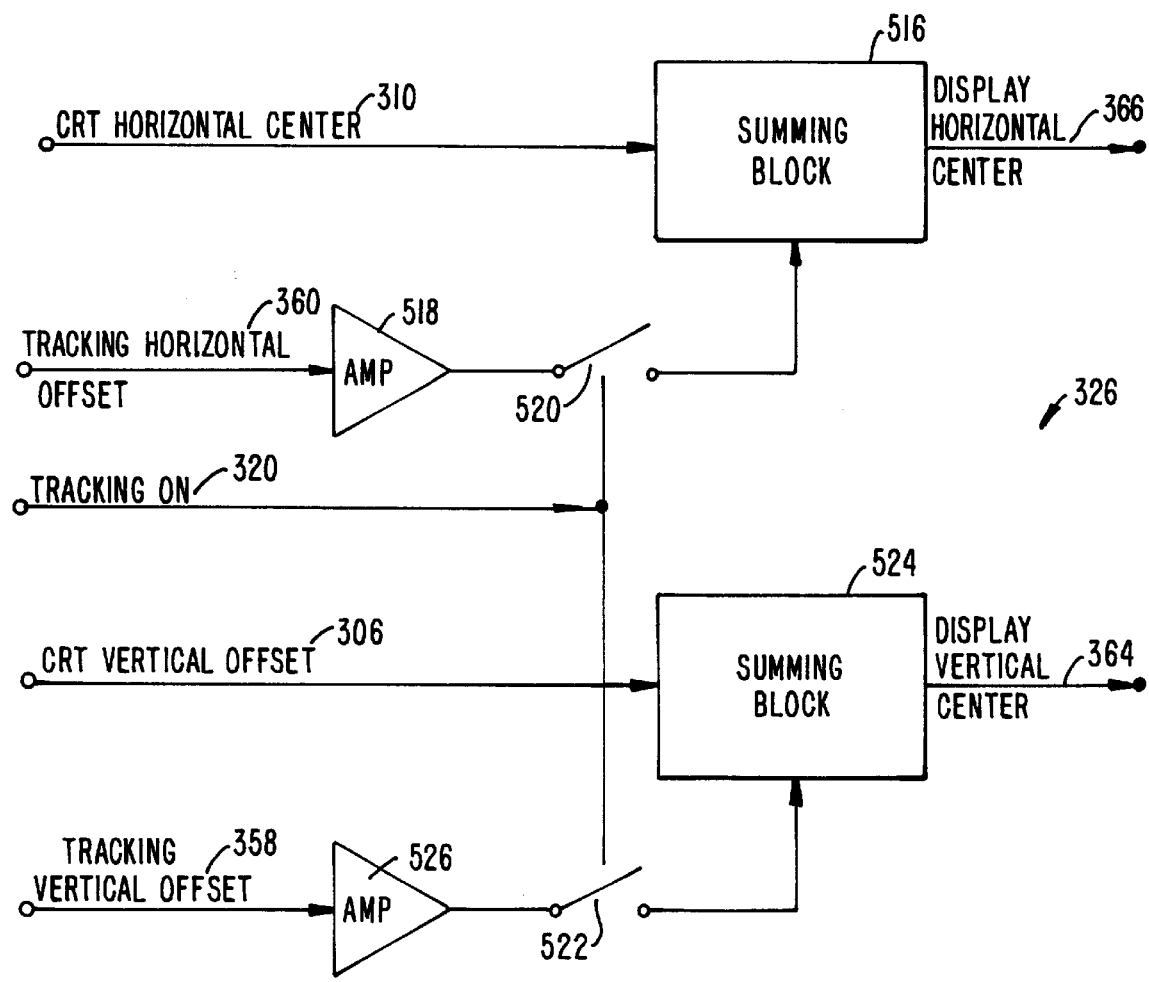
FIG. 15I is a block diagram illustrating a feedback circuit referred to in FIG. 15.

The feedback circuit 326 is schematically illustrated in FIG. 15i. The CRT horizontal center signal 310 is input to a summing block 516. The tracking horizontal offset 360 is input to an amplifier 518. The output of amplifier 518 is input to a switch 520. The tracking on signal 320 is closes switches 520 and 522. The CRT vertical center signal 306 is input to summing block 524. The tracking vertical offset 358 is input to an amplifier 526. The output of amplifier 526 is input to switch 522. When the tracking on signal 320 is active, the summing block 516 adds the output of amplifier 518 with the CRT horizontal center signal 310. The output of summing block 516 is the display horizontal center signal 366. Also, when the tracking on signal 320 is active, the output of amplifier 526 is added with the CRT vertical center signal 306 by summing block 524. The output of summing block 524 is the display vertical center signal 364.

Figure 15J:
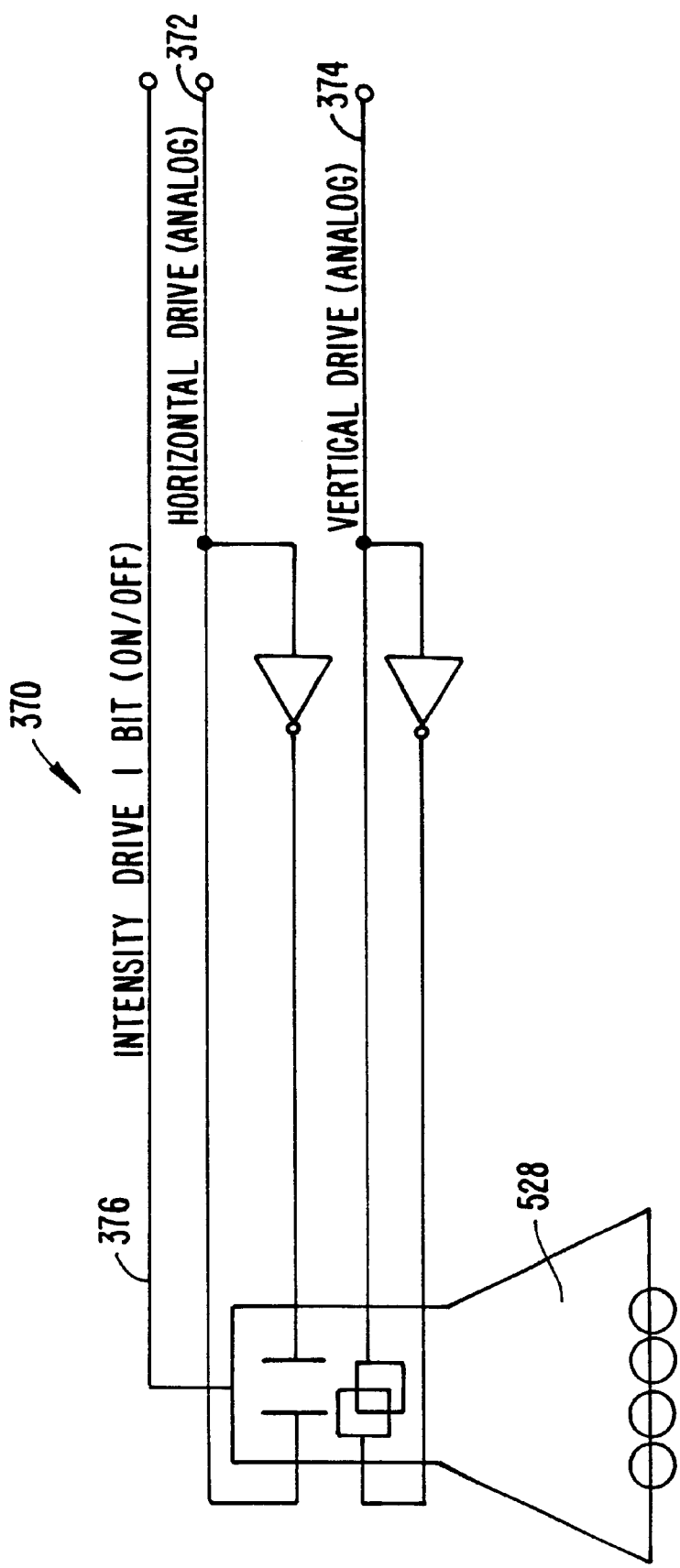
FIG. 15J is a block diagram illustrating a CRT circuit referred to in FIG. 15.

The CRT circuit 370 is schematically illustrated in FIG. 15J. An intensity drive signal 376 is input to a CRT for controlling the intensity. A horizontal drive 372 is connected to the CRT for controlling the horizontal position of the scanning spot. A vertical drive 374 is input to the CRT for controlling the vertical position of the scanning spot.

Figure 15K:
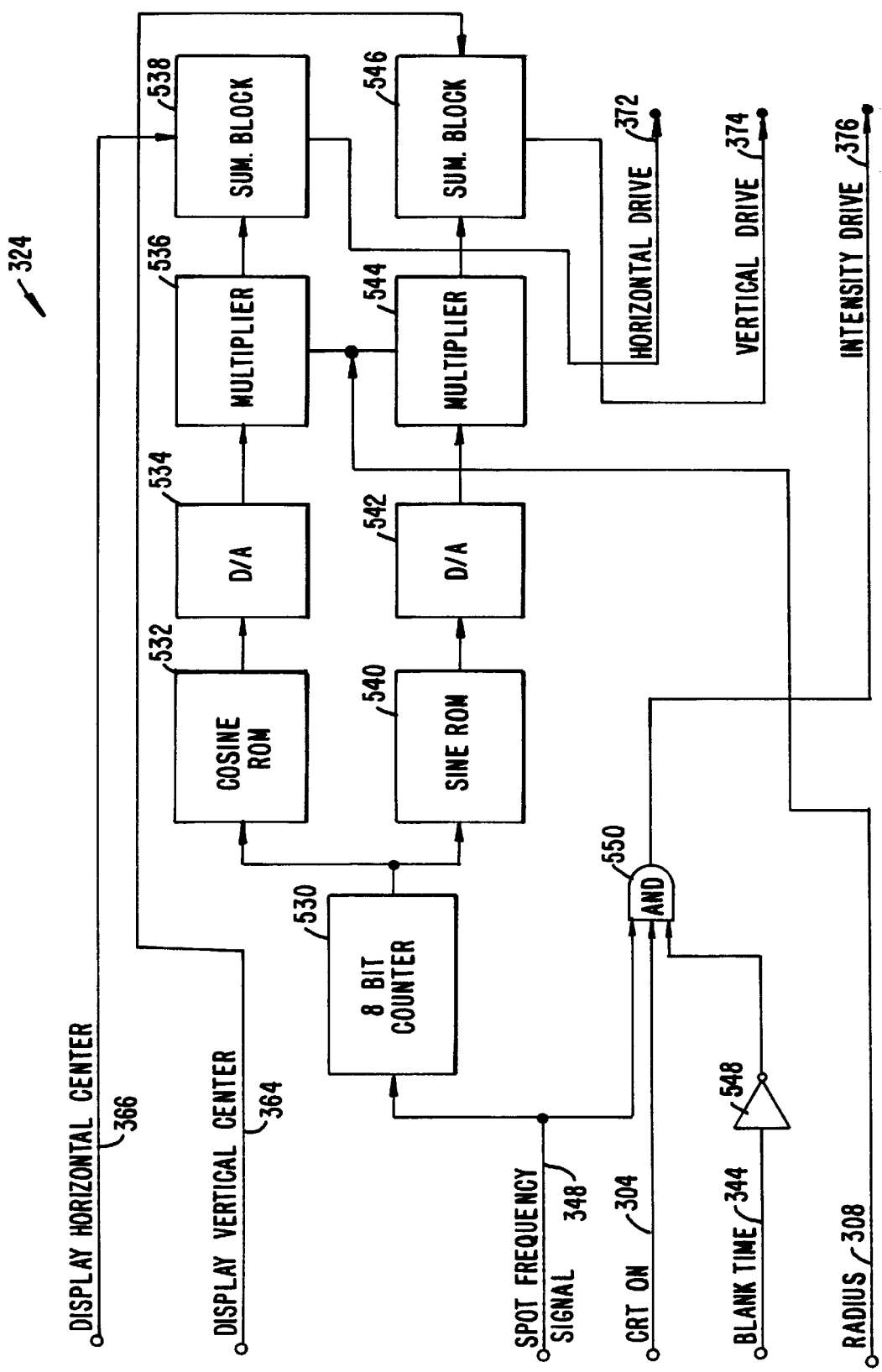
FIG. 15K is a block diagram illustrating a circle generator circuit referred to in FIG. 15.

The circle generator circuit 324 is schematically illustrated in FIG. 15k. The spot frequency signal 348 is input to an 8 bit counter 530. The output of the 8 bit counter 530 is input to a cosine ROM 532. The output of the cosine ROM 532 is input to a digital to analog converter 534. The output of the digital to analog converter 534 is input to a multiplier 536. The output of the multiplier 536 is input to a summing block 538. The display horizontal center signal 366 is input to the summing block 538. The output of summing block 538 is the horizontal drive 372. The output of the 8 bit counter 530 is also input to sine ROM 540. The output of sine ROM 540 is input to digital to analog converter 542. The output of digital to analog converter 542 is input to multiplier 544. The radius 308 is also input to the multiplier 544. The output from multiplier 544 is input to summing block 546. The display vertical center 364 is also input to the summing block 546. The output of the summing block 546 is the vertical drive 374. The blank time signal 344 is input to a NOT gate 548. The output of the NOT gate 548 is input to an AND gate 550. The spot frequency signal 348 and CRT on signal 304 are also input to the AND gate 550. The output of the AND gate 550 is intensity drive 376.

Figure 15L:
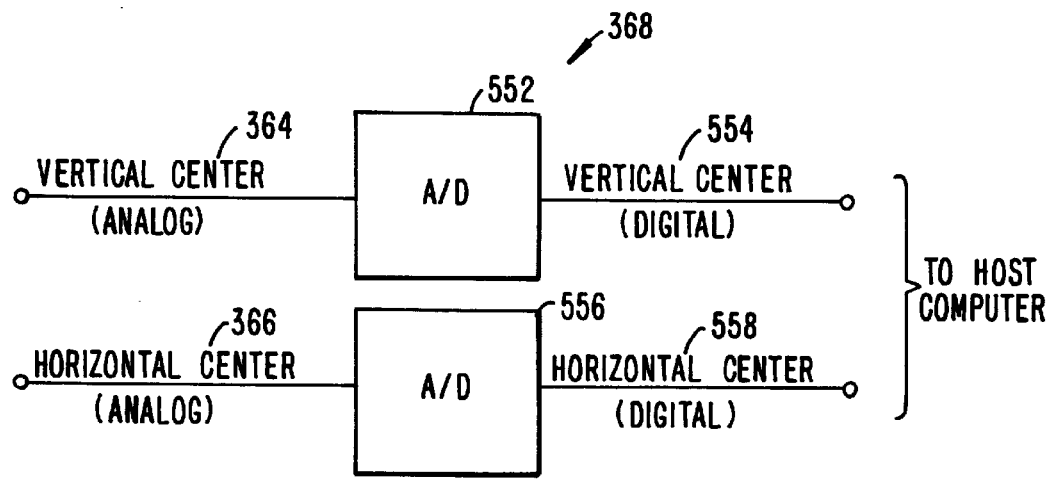
FIG. 15L is a block diagram illustrating a computer interface circuit referred to in FIG. 15.

The computer interface circuit 368 is schematically illustrated in FIG. 15l. The vertical center analog signal 364 is input to an analog to digital converter 552. The output of the analog to digital converter 552 is the digital vertical center 554. The horizontal center analog signal 366 is input to analog to digital converter 556. The output of analog to digital converter 556 is the digital horizontal center signal 558.

Figure 16:
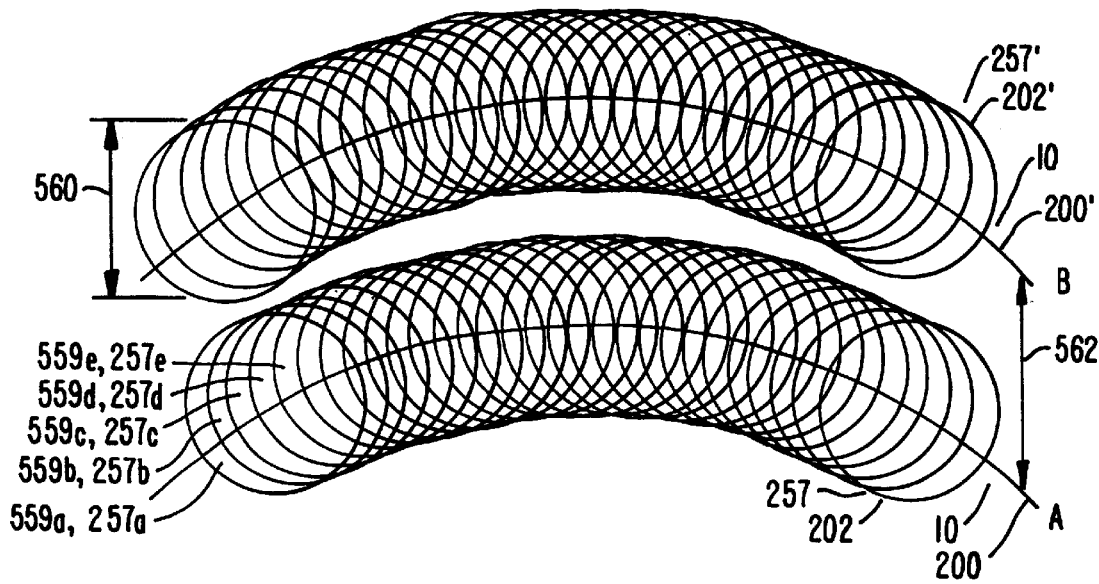
FIG. 16 is a schematic illustration of the overlapping of a pulsed scanning light spot that occurs while the light spot scans around a boundary in an embodiment of the invention.
Figure 17:
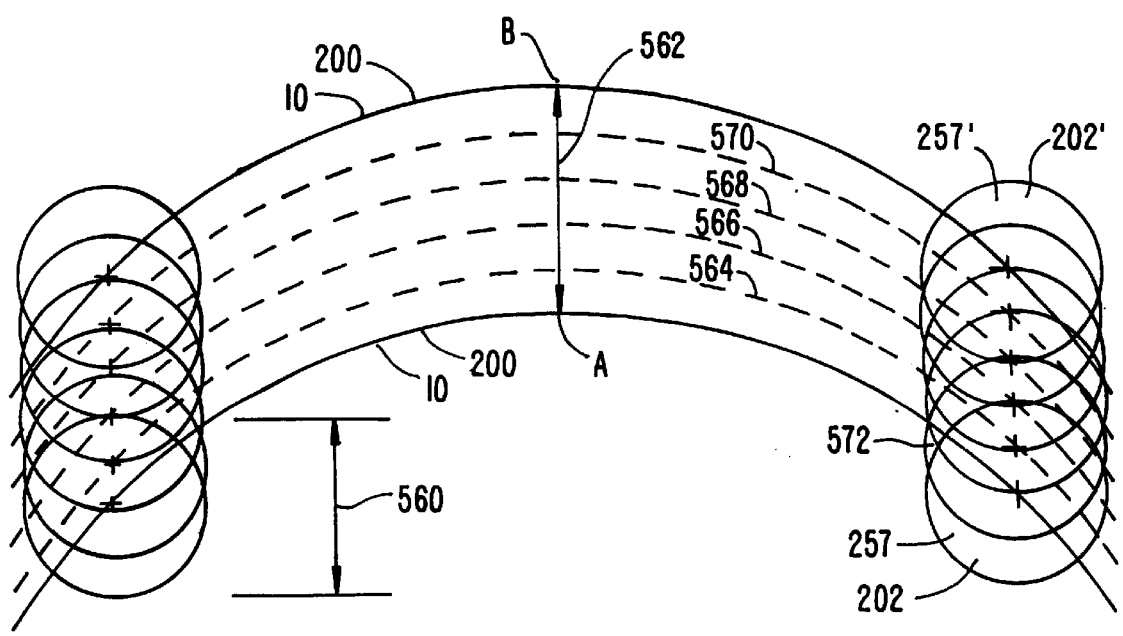
FIG. 17 is a schematic illustration of overlapping pulsed scanning light spots in which the trajectory of the spots is offset to match the displacement of an eye.

Referring now to FIGS. 14, 16 and 17, an alternate method for tracking the relative movement of the eye when the limbus of the eye is partially covered will now be described. The method includes automatically detecting the presence of a LASIK flap, pulsing and blanking the projection of a visible light spot, and displacing the trajectory 200 so that the position of the trajectory corresponds to the position of the eye as illustrated in FIGS. 14, 16 and 17. As illustrated above, this covering of the limbus may occur by an eyelid covering the limbus during normal viewing, or may occur during a surgical procedure such as LASIK. Once again, a visible light spot is projected so as to be confocal with a measured region on the eye. Alternatively, an infrared light spot may be projected so as to be confocal with a measured region of the eye. The measured region 257 and light spot 202 are scanned around the eye as illustrated in FIG. 14. The method also includes restricting a dimension across the measured region by selectively passing light rays from within the region to a light energy detector and excluding light rays from outside the region from the light energy detector. Further, a beam deflection module deflects the beam with a mirror, prism or lens. Alternatively, a light spot on a display may be projected onto the eye, and the projected light spot from the display scanned around the eye. The method encompasses scanning the light spot in an annular trajectory 200. A measured region 257 comprising a light spot 202 is sequentially scanned around a trajectory 200. The light spot 202 is turned off during a blanked portion 223 of the trajectory 200. The reflected light intensity is interpolated between measured values of the reflected light energy.

A limbus 10 of the eye 2 is initially positioned at A. The trajectory 200 is aligned with the limbus 10 at position A as illustrated in FIG. 16. The measured region 257 has a dimension 560 across the measured region. The eye 2 and the limbus 10 move so as to generate an offset of the limbus relative to the trajectory 200. The trajectory 200 is displaced from an initial position to the moved position of the limbus 10. Further motion of the limbus 10 will position the limbus at B. A displaced measured region 257' is sequentially scanned around a displaced trajectory 200' at position B. A separation distance 562 between positions A and B is greater than a dimension 560 across the measured region 257.

During the scanning of the visible light spot 202 around the trajectory 200, the light spot is pulsed. The desired frequency may range from 0.5 kHz to 500 kHz, and is preferably about 100 kHz. The light spot 202 is pulsed while scanning around the eye as illustrated in FIG. 16. The pulsing of the light spot will sequentially overlap positions of the maximum intensity light spots such as 559a through 559f around the trajectory 200. The sequentially measured regions such as 257a through 257f are formed by the pulsing of light spot 202 to form maximum intensity light spots such as 559a through 559f. The maximum intensity light spots overlap such that the measured regions comprising the spots will overlap. For example, a measured region such as 257c will overlap with adjacent measured regions 257a, 257b, 257d and 257e. The pulsing of the light spot 202 is synchronized with the scanning so that the number of pulses occurring during a rotation of the light spot 202 around the trajectory 200 remains constant.

Each rotation around the trajectory has a first pulse, and the angular separation of a sequentially occurring pulse remains fixed relative to the first pulse of the rotation around the trajectory. Each rotation of the light beam 202 around the trajectory 200 will generate a signal at a reference frequency, the reference frequency being the same frequency as the rotation of the spot 202 around the trajectory 200. This reference frequency may also be referred to as the spinning frequency at which the beam spins around the trajectory 200.

The pulsing of the light spot 202 will produce a carrier signal at the frequency of the pulsing light spot. The carrier signal is amplitude modulated by the light reflected from measured region 257 as the measured region 257 and light spot 202 rotate around the trajectory 200. Demodulating the amplitude modulated signal at the carrier frequency will produce a signal with AC and DC components. A varying AC component will occur at the reference frequency and a DC component will occur that corresponds to the average reflected intensity. A phase angle of the varying AC component is compared to the reference to determine an angle of the eye displacement. The magnitude of the varying signal is compared to the reference to determine the magnitude of the eye displacement.

As the limbus 10 moves from position A to position B, the scanning is performed such that the limbus 10 remains within at least a portion of the measured region 257 as illustrated in FIG. 17. For example, the limbus 10 is initially positioned at A and aligned with the trajectory 200. Displacement of the limbus 10 to position 564 will cause a slight misalignment of the limbus 10 with the trajectory 200. This slight misalignment causes a varying signal at the reference frequency. By comparing an amplitude and a phase of the varying signal with a reference, the position of the eye relative to the trajectory 200 is determined. The trajectory 200 displaces so as to be aligned with the displaced position 564 of the limbus 10. Further motion of the limbus 10 to displaced position 566 will cause the trajectory 200 to displace further and align with the displaced position 566 of the limbus 10. This alignment of the trajectory 200 with the displaced position 566 of the limbus 10 minimizes the variation in intensity of reflected light energy. During the displacing of the limbus 10, the trajectory 200 offsets and aligns with the limbus before the limbus 10 moves outside the measured region 257.

Figure 18:
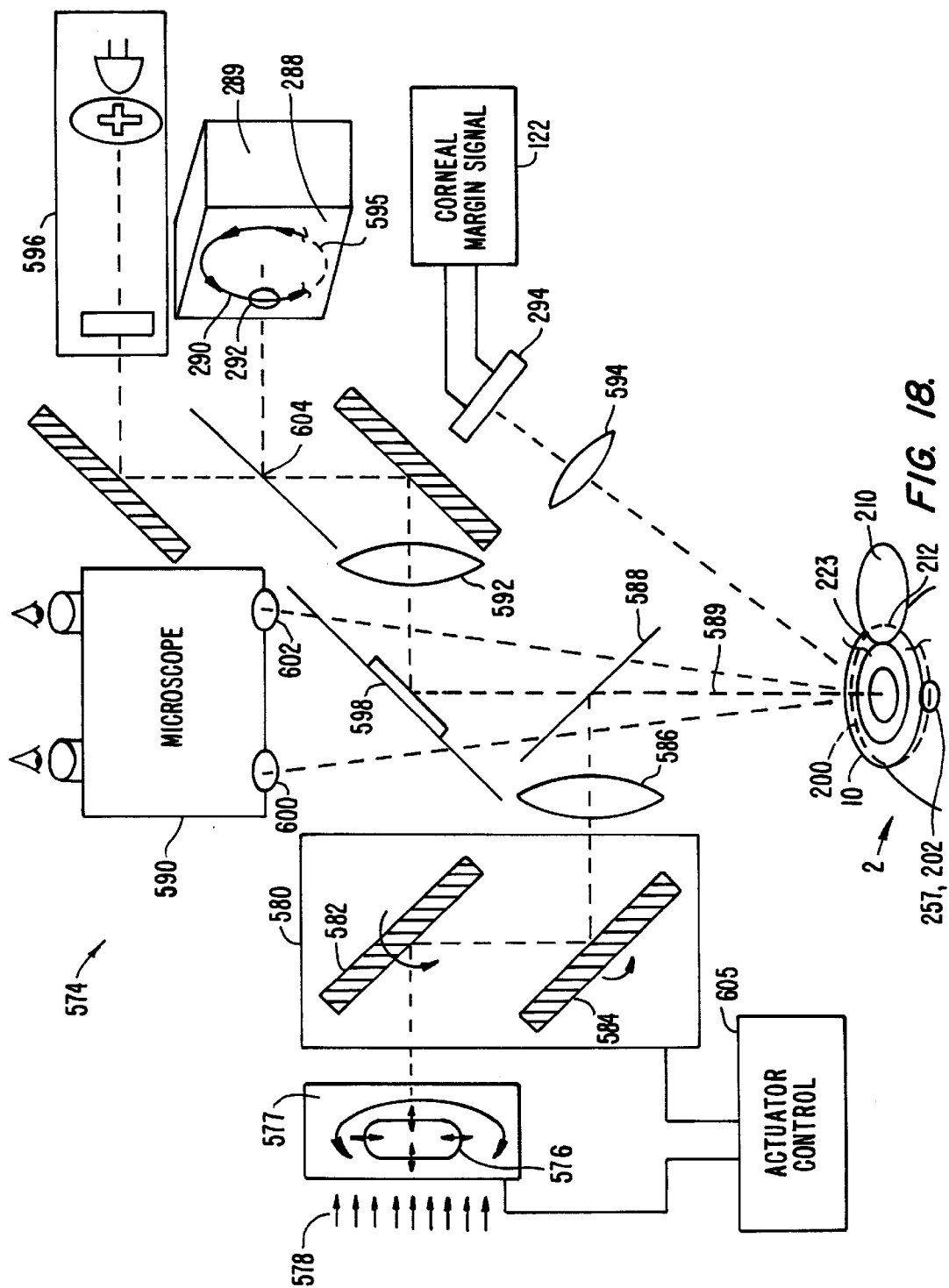
FIG. 18 is a schematic illustration of an embodiment of the invention including an eye tracker integrated with a laser surgery system.

In an exemplary embodiment, the eye tracker is integrated with a scanning laser surgery system as illustrated in FIG. 18. The laser system 574 is used to sculpt the anterior surface of an eye to a predetermined shape. The scanning laser delivery system 574 includes a laser beam shaping module 577 positioned in the path of an ablative laser beam 578. The laser beam shaping module 577 selectively passes the laser beam through a variable aperture 576. A dimension of variable aperture 576 is changed between pulses of the laser beam 578 to vary the shape of the laser beam on the eye. The beam shaping module 577 may be rotated so as to rotate the variable aperture 576 about the eye 2. The laser beam shaping module 577 is controlled by actuator control circuitry 605. The scanning laser system 574 further includes a laser beam deflection module 580 that is used to offset the laser beam path between pulses of the laser beam 578. The beam deflection module 580 includes two rotating mirrors 582 and 584 for moving the position of the laser beam path. The beam deflection module 580 further includes appropriate mechanical actuators for moving the mirrors. Alternatively, the beam deflection module may include other optical elements for deflecting the laser beam such as movable prisms and lenses.

The mechanical actuators of beam deflection module 580 are controlled by actuator control circuitry 605. An imaging lens 586 is positioned in the laser beam path. The imaging lens 586 forms and image of the aperture 576 near the eye. A beam splitter 588 selectively reflects the laser beam energy, and transmits visible and near infrared light energy to an operating microscope 590.

The eye tracking subsystem includes a scanning light spot 292 from a screen 288 of a cathode ray tube 289 that is projected onto the eye. The light spot 292 travels around a trajectory 290 on the cathode ray tube screen. Although a cathode ray tube is used, any suitable display such as a super luminescent display, liquid crystal display or active matrix display may also be used. An imaging lens 592 is positioned to project the spot 292 on the eye 2. A beam splitter 588 couples the eye tracking system with the laser delivery system. A light collection lens 594 is positioned in front of a light detector 294. The light collection lens 594 preferably images the eye 2 onto the detector 294. The reflected light is converted to electrical corneal margin signal 122 by the detector 294.

The presence of the flap 210 is automatically detected as described above. During a portion of the scanning of the measured region 257 around the trajectory 202, the light spot 202 is turned off over a blanked portion 223 of the trajectory 200. The blanked portion 595 of the video trajectory 290 corresponds to the blanked portion 223 of the trajectory 200. This blanked region provides visual feedback to the surgeon that the overlying flap of tissue has been accurately detected.

Other elements are preferably integrated with laser surgery system 574 such as an operating microscope 590 and a visual fixation target system 596. A mirror 598 is positioned between the objective lens apertures 600 and 602 of the microscope 590. The mirror 598 reflects light from the eye tracking and visual fixation target system toward the eye 2. Microscope 590 preferably permits viewing of the trajectory 200 of measured region 257 around eye 2. A beam splitter 604 selectively reflects light of predetermined wavelengths from CRT screen 288, and selectively passes light of predetermined wavelengths from visual fixation system 596. Visual fixation system 596 provides a target for the patient to view during surgery. Although this embodiment of the invention employs an eye tracker including a scanning spot from a CRT screen, alternate embodiments of the invention will include other suitable methods for scanning a measured region 257 as illustrated above.

Figure 18A:
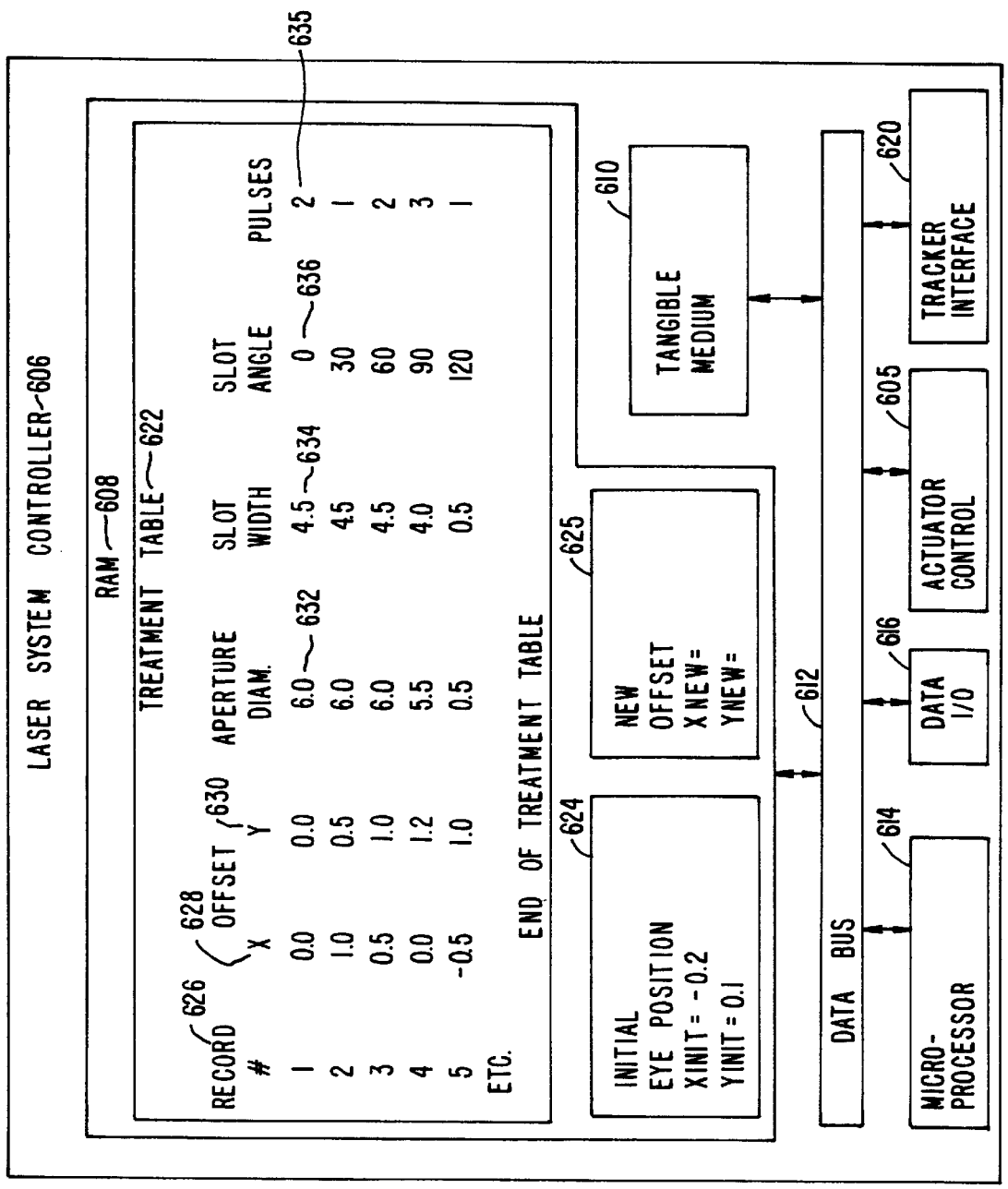
FIG. 18A is a block diagram that illustrates a laser system controller of the invention used to control the laser system of FIG. 18.

The laser system 574 includes a laser system controller as illustrated in FIG. 18a. The laser system controller 606 includes a random access memory (RAM) 608, a tangible medium 610, a data bus 612, a microprocessor 614, a data port 616, an actuator control circuit 605 and an eye tracker interface 620. The tangible medium may comprise any suitable computer readable medium such as read only memory (ROM), a floppy or hard disk drive, or the like.

The RAM is configured to include a laser treatment table 622 that is at least partially stored in the RAM during the laser treatment. Preferably, the entire laser treatment table is stored in RAM prior to treatment to avoid delays caused by calculating the laser treatment during the laser treatment. The eye tracker interface 620 inputs the position of the eye to the laser system controller 606. An initial eye position 624 is stored in the RAM 608 at the start of the laser treatment. The laser treatment table 622 includes numbers corresponding to the positions and shapes of the laser beam 578 on the eye during the pulsing of the laser. The laser treatment table includes several records 626. The records in the laser treatment table list the configuration of the laser during discrete pulses of the laser beam. The laser treatment table 622 includes fields for an X offset 628 and a Y offset 630 of the laser beam from a laser treatment center. In this laser treatment table the offsets are listed as X and Y coordinates relative to the treatment center, but any suitable coordinate system may be used. The treatment table also includes fields for the variable aperture diameter 632, the variable aperture slot width 634 and the variable aperture slot angle 636. The laser treatment table 622 also includes a field for the number of pulses 635 for each record 626 of the laser treatment table 622.

Figure 18B:
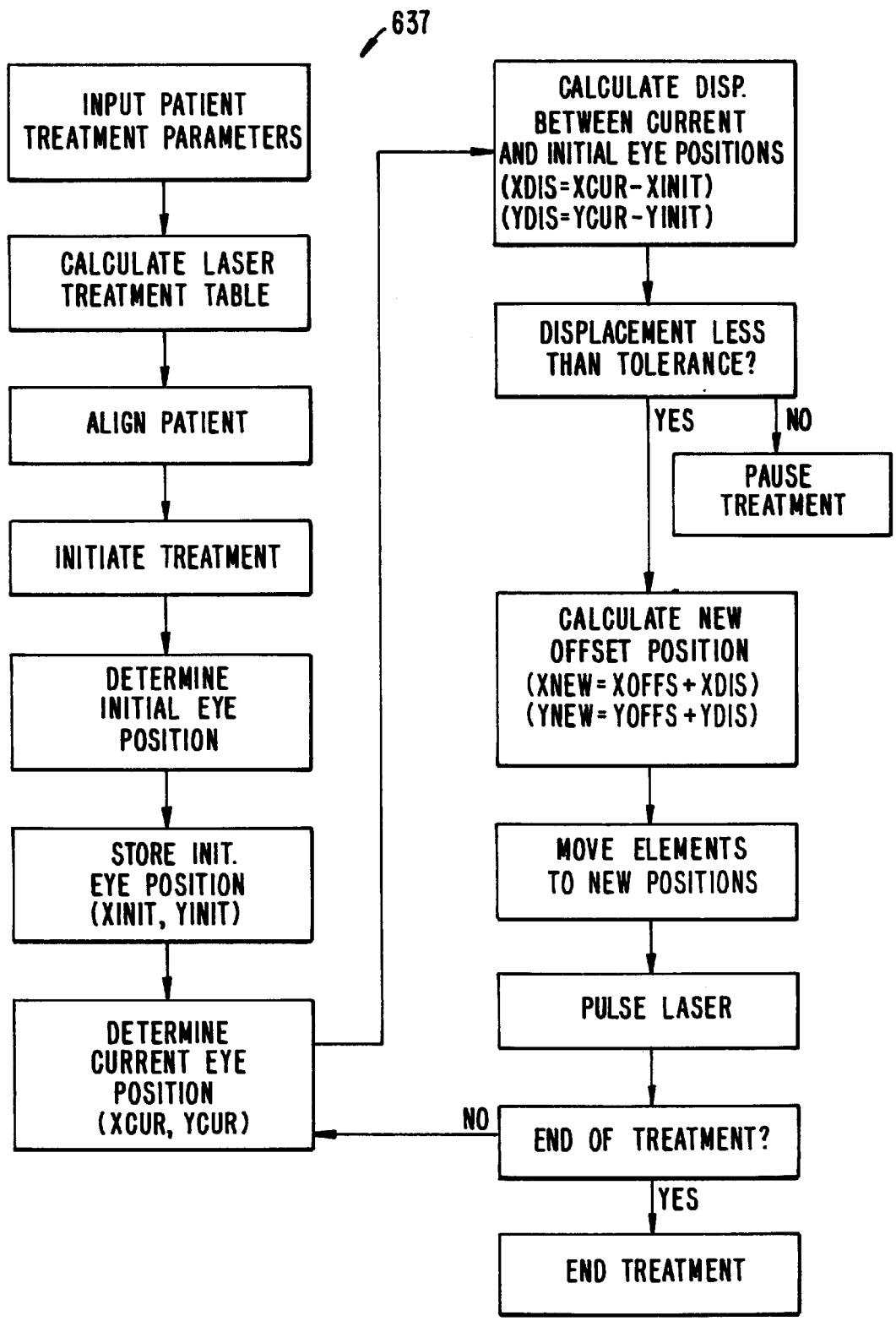
FIG. 18B is a block diagram that illustrates a computer routine of the invention for use with the laser system controller of FIG. 18A.

A flow chart illustrating a computer routine 637 for treating the patient with a laser beam is shown in FIG. 18b. The routine includes input of the patient laser treatment parameters such as the patient eyeglass prescription. These parameters are input into the laser system controller 606 via data I/O port 616 and stored in RAM 608. The laser system controller calculates the laser treatment table 622 and stores the table in the RAM 608. A surgeon aligns the eye 2 of the patient with the laser system 574. By activating a switch or other input device, the surgeon then indicates that the patient is aligned.

The surgeon initiates the laser treatment by depressing a foot switch or other input device. Alternatively, by initiating the laser treatment, the surgeon may indicate that the patient is aligned. The eye tracker determines the initial eye position 624 when the surgeon indicates that the patient is aligned. The initial eye position 624 is stored in the computer RAM as illustrated by the variables XINIT and YINIT corresponding to the initial X and Y coordinate positions of the eye. These coordinate positions of the eye are preferably away from the laser treatment center. The current position of the eye is determined by accessing the tracker interface port 620.

The current position of the eye is stored in RAM as illustrated by the variables XCUR and YCUR corresponding to the current X and Y coordinate positions of the eye. For the first laser pulse the initial position of the eye may be considered the current eye position. The displacement vector between the initial position of the eye and the current position of the eye may be illustratively represented by the variables XDIS and YDIS for the X and Y displacements respectively. The values of XDIS and YDIS are calculated by subtracting the initial position designated by the coordinate reference (XINIT, YINIT) from the current position of the eye designated by the coordinate reference (XCUR, YCUR). The displacement vector designated by the coordinate reference (XDIS, YDIS) is compared to a threshold tolerance. If the displacement vector is greater than the tolerance, the treatment is paused and an alarm may be activated. If the displacement vector is less than the threshold, the displacement vector between the initial and current eye positions is used to calculate the new offset position for the next laser pulse.

The new X and Y offset positions are designated by the coordinate reference (XNEW, YNEW). The values of XNEW and YNEW are calculated by adding the displacement vector (XDIS, YDIS) to the original offset position (XOFFS, YOFFS) of the current record in the treatment table 622. The laser elements are configured as indicated by the current record of the treatment table and the new X and Y offset positions XNEW and YNEW respectively. The laser is pulsed. The computer routines for determining the current eye position through the computer routine for pulsing the laser are repeated until the last pulse indicated by the treatment table has been delivered as illustrated in FIG. 18b.

Figure 19:
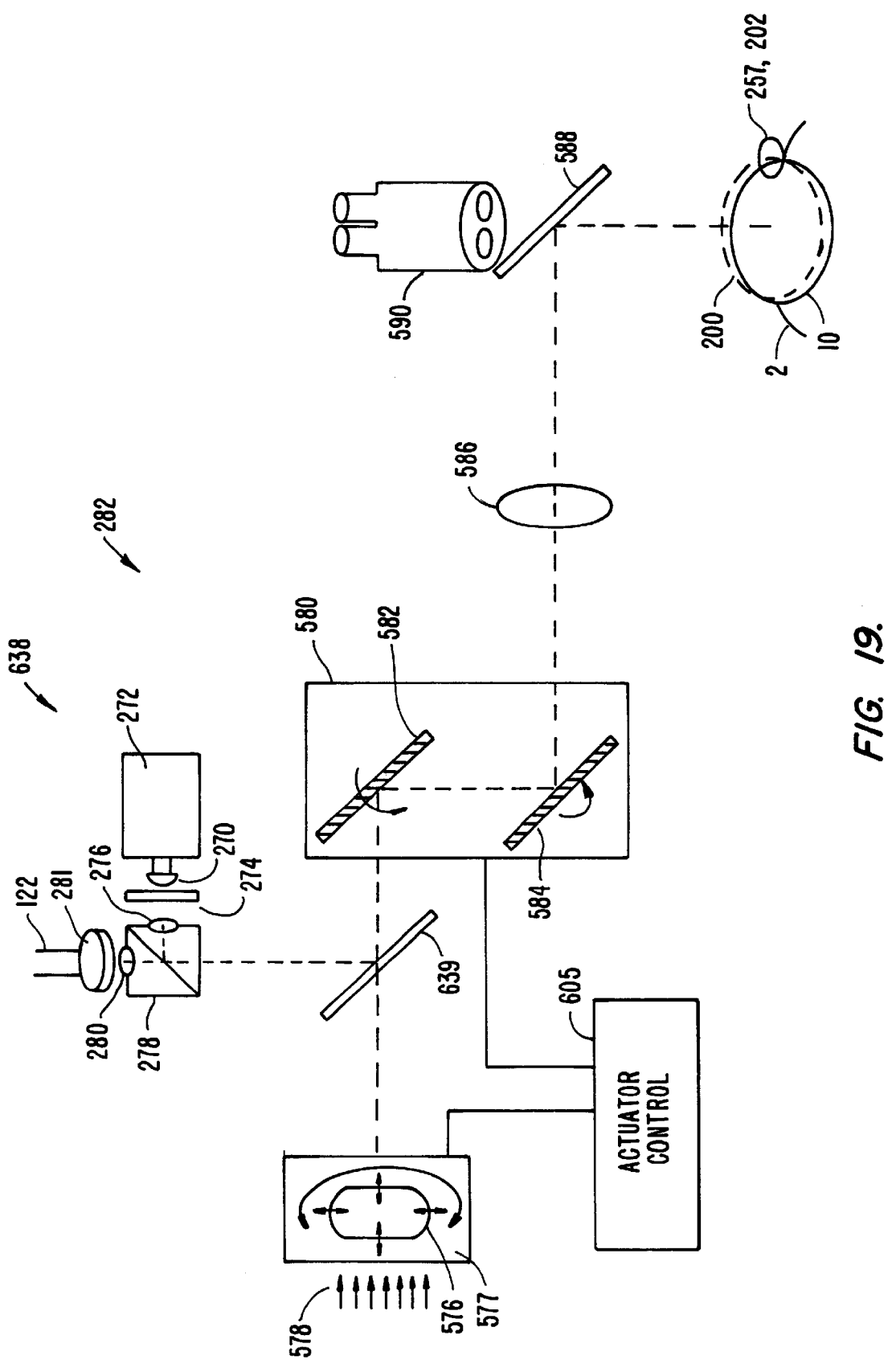
FIG. 19 is a schematic illustration of an embodiment of the invention using the same beam deflection module to deflect both a scanning laser treatment beam and light beam for measuring the position of an eye.

In an alternate embodiment of an eye tracker integrated with a scanning laser system, the beam deflection module of the scanning laser system may be used to scan the measured region 257 around a trajectory 200 as illustrated in FIG. 19. The integrated system 638 includes a laser beam shaping module 577 for defining a variable aperture 576, a laser beam 578, and a laser beam deflection element 580 that is used to offset the laser beam path. The laser beam deflection element 580 is also used to scan the measured area 27 around a trajectory 200.

A beam splitter 639 intercepts laser beam 578 and pulsed light from light source 270. The beam splitter 639 selectively passes laser beam 270 and reflects pulsed light from light source 270. Alternatively, the beam splitter 639 may selectively reflect laser beam 270 and pass light from light source 274. The beam splitter 639 aligns the apertures 276 and 280 with variable aperture 576. The apertures 576, 276 and 280 are concentric when imaged onto the eye 2. As the laser treatment proceeds, the image of variable aperture 276 is scanned according to the laser treatment table 622. Between pulses of the laser beam 578, the apertures 276 and 280 scan the measured region 257 around a trajectory 200.

Figure 21:
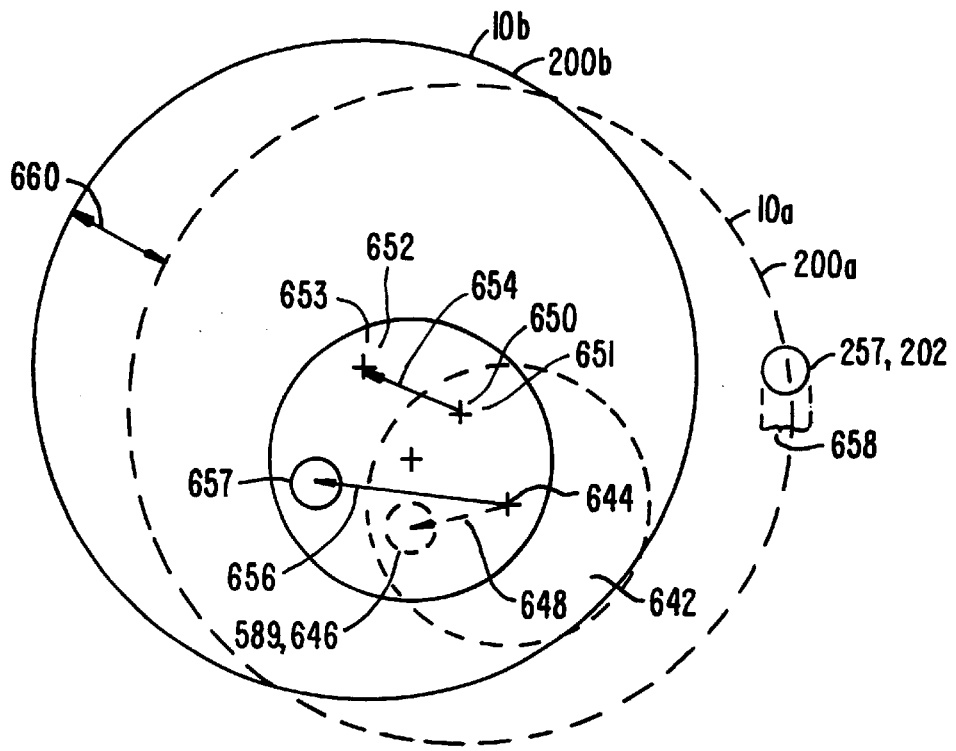
FIGS. 20 and 21 are schematic illustrations of method of ablating a moving eye with a laser beam.
Figure 20:
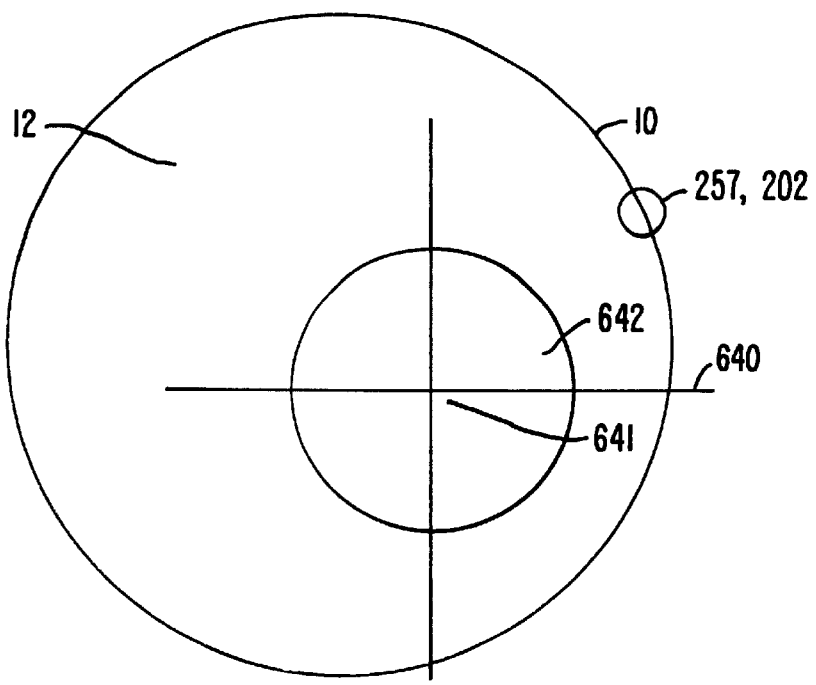

A method of ablating a moving eye with a laser system such as 574 is illustrated in FIGS. 20 and 21. The eye is laser sculpted to a predetermined shape with a series of pulses from a beam of an ablative laser energy. A reticule 640 indicates the center 641 of an intended laser treatment area 642. The intended laser treatment area 642 is aligned so as to ablate the cornea 12 to a desired shape within the intended laser treatment area 642. The position of the eye is determined with a scanning light spot 202 as described above. An initial trajectory 200a of the scanning light spot 202 and the scanning measured region 257 is aligned with the initial position of the limbus 10a. An intended laser treatment area 642 is aligned relative to an initial position of a limbus 10a. A LASIK flap of excised tissue that covers the limbus is automatically detected, and the visible light beam is blanked over the flap as described above. An intended laser treatment area 642 is eccentric with the limbus 10a as illustrated in FIG. 20. The intended laser treatment area 642 is to be treated with a plurality of individual laser pulses such as individual laser pulse 646. The offset laser beam path 589 is offset during the laser beam pulse 646. The individual laser pulses are of varying size and offset position as indicated by the laser treatment table 622. The laser treatment table 622 lists the intended offset positions of the laser beam relative to a reference position 644. The reference position 644 is preferably located at the center 641 of the intended treatment area 642, but may alternatively be located away from the center 641 of the intended treatment area 642. An intended offset vector 648 illustrates the intended offset position of a single laser beam pulse 646 relative to the reference 644. The intended offset vector 648 will comprise both an X offset 628 and a Y offset 630 position of the treatment table 622.

During laser surgery, the eye will typically move between the time the patient is aligned with the laser and the time at which a laser pulse is delivered. A moved limbus 10b of the eye is aligned with a moved trajectory 200b. A separation distance 660 between the initial limbus position 10a and a moved limbus position 10b exceeds a dimension 658 across the measured region 257. The eye tracker axis and laser beam path are independently movable. An initial position of the axis of the eye tracker 651 is displaced to a current position of the axis of the eye tracker 653.

When the patient is aligned with the laser, an initial position of the eye 650 is determined. The initial position of the eye 650 is stored in the RAM 608 of the laser system controller 606. Prior to ablating an intended individual laser pulse such as 646, a current position of the eye 652 is determined. An eye displacement vector 654 is calculated by subtracting the initial eye position 650 from the current eye position 652. The eye displacement vector 654 is compared to a maximum displacement tolerance. If the displacement vector 654 is greater than the tolerance, the laser system controller 606 pauses the laser treatment. If the displacement vector 654 is less than the maximum displacement tolerance, the laser system controller 606 calculates a new offset position 656 based on the X offset 628 and Y offset 630 positions of the current record 626 of the treatment table 622. The laser beam shaping and offset elements move to the new positions indicated by the new offset position 656 and the other fields 632 to 636 of the current record of the laser treatment table. The current record of the laser treatment table could be any record of the laser treatment table such as record number 4. The laser beam 578 is pulsed according to the pulses field 635 of the current record of the laser treatment table 622.

After the laser is pulsed, the step of determining the current position of the eye and the subsequent steps leading to the pulsing of the laser beam 578 are repeated. After all of the laser pulses indicated by the treatment table 622 have been delivered, the laser treatment is ended.

It should be understood that although the present invention has generally been described in use with a scanning laser system including an ultraviolet laser for ablating a surface of an eye, the invention is not limited to this type of system. For example, the systems and methods described herein may be employed in conjunction with a laser system employing other suitable wavelengths of electromagnetic radiation such as electromagnetic radiation from the infrared portion of the spectrum of electromagnetic radiation. While the above is a complete description of the preferred embodiments of the invention, various alternatives, modifications, and equivalents may be used. For example, the present invention might be used with a scanning laser system, such as the T-PRK$^R$ scanning and tracking laser from Autonomous Technologies Corporation or the Keracor™ 217 scanning laser system from Chiron Vision, as well as with large area ablation laser systems. Therefore, the above description should not be taken as limiting the scope of the invention which is defined by the appended claims.

What is claimed is:

1. A method for tracking movement of the eye of a patient comprising:
   directing a light beam at a region of the eye including portions of the sclera and the iris;
   receiving reflected light from said region of the eye; and
   measuring an intensity of the reflected light to determine a relative position of the eye.

2. A method for tracking movement of the eye of a patient comprising:
   directing a light beam at a region of the eve including portions of the sclera and the iris, the light beam defining an annular light pattern directed onto the eye radially outward from the pupil;
   receiving reflected light from said region of the eye; and
   measuring an intensity of the reflected light by measuring signals corresponding to light intensity of reflected light from discrete portions of the annular light pattern to determine a relative position of the eye.

3. The method of claim 1 further comprising:
   scanning a light spot along a substantially annular trajectory radially outward from the pupil; and
   measuring signals corresponding to light intensity of reflected light from discrete portions of the annular trajectory to determine a relative position of the eye.

4. The method of claim 1 wherein the reflected light includes light reflected from the sclera having a first intensity and light reflected from the iris having a second intensity less than the first intensity.

5. The method of claim 1 wherein the region of the eye is an annular region disposed radially outward from the pupil adjacent to or near the limbus between the sclera and the iris.

6. A method for tracking movement of the eye of a patient comprising:
   directing a light beam at a region of the eye including portions of the sclera and the iris, wherein the region of the eye is an annular region disposed radially outward from the pupil adjacent to or near the limbus between the sclera and the iris;
   receiving reflected light from said region of the eye;
   measuring an intensity of the reflected light to determine a relative position of the eye; and
   determining a position of the limbus relative to the annular region based on the intensity of the reflected light.

7. A method for tracking movement of the eye of a patient comprising:
   directing a light ray at a region of the eye radially outward from the pupil;
   scanning the light ray in an annular trajectory around the pupil; and
   measuring signals corresponding to light intensity of reflected light from the annular trajectory to determine a relative position of the eye.

8. The method of claim 7 further comprising positioning the annular trajectory region adjacent to or near the limbus between the sclera and the iris and scanning the light ray around the limbus to determine a reference intensity signal.

9. The method of claim 8 further comprising tracking subsequent movement of the limbus relative to the annular trajectory by measuring changes in the intensity of the reflected light.

10. The method of claim 7 wherein the light ray is scanned around the annular trajectory at a reference frequency, the method further comprising:
    generating an alternating current component of the reference frequency;
    comparing an amplitude of the light ray signals with an amplitude of the reference frequency to determine a magnitude of eye displacement.

11. The method of claim 7 wherein the light ray is scanned around the annular trajectory at a reference frequency, the method further comprising:
    generating an alternating current component of the reference frequency; and
    comparing a phase of the light ray signals with a phase of the reference frequency signal to determine a vector angle of eye displacement.

12. The method of claim 7 wherein the light ray is scanned around the annular trajectory by oscillating mirrors positioned between a light source and the eye.

13. The method of claim 7 further comprising sequentially activating a ring of light sources to sequentially scan light rays around the annular trajectory.

14. The method of claim 7 further comprising transmitting light through one or more optical fibers to the eye and rotating a distal end portion of the optical fibers to scan the light around the annular trajectory.

15. The method of claim 7 wherein the light has a wavelength in the infrared region.

16. A method for performing a surgical procedure on the eye comprising:
    applying energy to a tissue structure on the cornea;
    during the applying step, directing light at or near the limbus and receiving reflected light from said limbus;
    measuring an intensity of the reflected light to determine a relative position of the limbus; and
    modifying the applying step based on said position of the limbus.

17. The method of claim 16 further comprising:
    directing an annular light pattern onto the eye radially outward from the pupil; and
    measuring signals corresponding to light intensity of reflected light from discrete portions of the annular light pattern to determine a relative position of the eye.

18. The method of claim 16 further comprising:
    scanning a light spot along a substantially annular trajectory radially outward from the pupil; and
    measuring signals corresponding to light intensity of reflected light from discrete portions of the annular trajectory to determine a relative position of the eye.

19. The method of claim 16 wherein the applying energy step comprises projecting ultraviolet radiation onto the cornea to ablate a tissue structure on the optically useful portion of the anterior surface of the cornea.

20. The method of claim 19 wherein said cornea comprises an epithelium, a Bowman's layer and a stroma, the method further comprising removing the epithelium and at least a portion of the Bowman's layer from the anterior region of the cornea to expose a selected region of the stroma and ablating a portion of the stroma within the selected region.

21. The method of claim 16 further comprising:
    before the applying energy step, removing a region of tissue including portions of the limbus to expose an underlying region of the cornea that is substantially non-reflective;
    scanning a light ray along a substantially annular trajectory, the annular trajectory including at least a portion of the non-reflective underlying portion of the cornea and a reflective portion of the eye that has not been removed; and interpolating a position of the limbus relative to the annular trajectory based on the intensity of the reflected light from said reflective portion of the eye.

22. An optical system for tracking movement of the eye of a patient comprising:
    a light source;
    an optical train for directing a light ray from the light source at a region of the eye including the sclera and the iris;
    a light detector positioned to receive reflected light from said region of the eye; and
    a controller coupled to the light detector for measuring an intensity of the reflected light to determine a relative position of the eye.

23. An optical system for tracking movement of the eye of a patient comprising:
    a light source;
    an optical train for directing a light ray from the light source at a region of the eye including the sclera and the iris;
    a light direction system positioned along the optical train, the light direction system being configured to scan the light ray in an annular trajectory around the pupil of the eye;
    a light detector positioned to receive reflected light from said region of the eye; and
    a controller coupled to the light detector for measuring an intensity of the reflected light to determine a relative position of the eye, the controller comprising an electrical system coupled to the light detector and configured to measure signals corresponding to light intensity of reflected light from discrete portions of the annular trajectory.

24. The optical system of claim 23 wherein the light direction system comprises oscillating mirrors positioned between the light source and the eye and a motor for oscillating the mirrors such that the light is scanned around the annular trajectory.

25. The optical system of claim 23 wherein the light direction system comprises a ring of light sources positioned in an annular array such that sequential activation of the light sources causes light to scan around the annular trajectory.

26. The optical system of claim 23 wherein the light direction system comprises one or more optical fibers coupled to the light source for transmitting light therethrough, the optical fibers having an end portion for projecting light onto the eye, and a drive for rotating the end portion of the optical fibers to scan the light around the annular trajectory.

27. The optical system of claim 23 further comprising a calibration system coupled to the light direction system for positioning the annular trajectory substantially coincident with the limbus.

28. The optical system of claim 23 further comprising a reference synchronization system for scanning a light ray onto a reference light detector at a reference frequency and a reference intensity, and an electrical system for generating an alternating signal having a reference phase and a reference amplitude based on the reference frequency and the reference intensity.

29. The optical system of claim 28 wherein the electrical system is coupled to the light detector for generating a corneal margin signal having a corneal margin phase and a corneal margin amplitude based on a phase and an amplitude of signals from the reflected light, the electrical system further comprising a phase comparator for comparing the phase of the reflected light signal with the reference phase to determine a vector angle of eye displacement, and an amplitude comparator for comparing the amplitude of the reflected light signal with the reference amplitude to determine a magnitude of eye displacement.

30. The optical system of claim 22 wherein the light source is configured to direct an annular light pattern onto the eye at or near the limbus, the controller comprising an electrical circuit coupled to the light detector for measuring signals corresponding to light intensity of reflected light from discrete portions of the annular light pattern.

31. An optical system comprising:
    a laser assembly for projecting radiation onto a selected region of the anterior surface of the cornea to effect ablation of said selected region to a certain depth; and
    an eye tracking system for tracking movement of the eye comprising:
        an optical system including a light source and a light direction system configured to scan a light ray in an annular trajectory around the pupil of the eye; and
        an electrical system coupled to the optical system and configured to measure signals corresponding to a light intensity of reflected light from discrete portions of the annular trajectory to track a position of the eye.

32. A method of tracking a position of an eye, the eye having a boundary, the method comprising:
    directing a light energy at the eye;
    measuring an intensity of the energy reflected from a region of the eye, the region including a portion of the boundary; and
    scanning the measured region around the eye to determine a position of the eye, the position being determined from a variation in the intensity of the reflected energy.

33. A method of tracking a position of an eye, the eye having a boundary, the method comprising:
    directing a light energy at the eye;
    measuring an intensity of the energy reflected from a region of the eye, the region including a portion of the boundary;
    restricting a dimension across the measured region by selectively passing light rays from within the region to a light energy detector and excluding light rays from outside the region from the light energy detector;
    scanning the measured region by rotating the measured region around the eye at a reference frequency in a pattern comprising an annular trajectory so as to generate a varying signal at the reference frequency to determine a position of the eye, the position being determined from a variation in the intensity of the reflected energy;
    comparing an amplitude of the varying signal with a reference to determine a magnitude of an eye displacement;
    comparing a phase angle of the varying signal with the reference so as to determine an angle of the position of the eye;
    positioning the trajectory to be substantially coincident with the boundary; and
    adjusting a first radius of the trajectory to match a second radius of the limbus.

34. A method of tracking a position of an eye, the eye having a boundary, the method comprising:

projecting a beam of light energy at the eye;

measuring an intensity of the energy reflected from a region of the eye, the region including a portion of the boundary and aligned with the beam; and scanning the beam and the region around the eye to determine a position of the eye, the position being determined from a variation in the intensity of the reflected energy.

35. A method of tracking a position of an eye, the eye having a boundary, the method comprising:

projecting a beam of light energy at the eye;

measuring an intensity of the energy reflected from a region of the eye, the region including a portion of the boundary and aligned with the beam;

restricting a dimension across the measured region by selectively passing light rays from within the region to a light energy detector and excluding light rays from outside the region from the light energy detector;

scanning the beam and the region by rotating the measured region around the eye at a reference frequency in a pattern comprising an annular trajectory so as to generate a varying signal at the reference frequency to determine a position of the eye, the position being determined from a variation in the intensity of the reflected energy;

comparing an amplitude of the varying signal with a reference to determine a magnitude of an eye displacement;

comparing a phase angle of the varying signal with the reference so as to determine an angle of the position of the eye;

positioning the trajectory to be substantially coincident with the boundary; and adjusting a first radius of the trajectory to match a second radius of the limbus.

36. A method for tracking a position of an eye, the eye having a boundary, the method comprising:

projecting a light beam comprising a light energy from a display onto the eye;

measuring an intensity of the energy reflected from a region of the eye, the region including a portion of the boundary; and scanning the beam around the eye to determine a position of the eye, the position being determined from a variation in the intensity of the reflected energy.

37. The method of claim 36 further comprising:

imaging the light beam to a focus at the region so as to more precisely define the region with the beam;

rotating the beam around the eye at a reference frequency in a pattern comprising an annular trajectory so as to generate a varying signal at the reference frequency;

comparing an amplitude of the varying signal with a reference to determine a magnitude of an eye displacement;

comparing a phase angle of the varying signal with the reference so as to determine an angle of the position of the eye;

positioning the trajectory to be substantially coincident with the boundary; and adjusting a first radius of the trajectory to match a second radius of the limbus.

38. A method for tracking a position of an eye during surgery, the eye having a limbus, the method comprising:

directing a light energy at the eye;

measuring an intensity of the energy reflected from a region of the eye, the region including a portion of the limbus; and automatically detecting a flap of excised tissue covering the limbus.

39. The method of claim 38 further comprising:

projecting a visible light beam onto the region;

imaging the light beam to a focus at the region so as to more precisely define the region with the beam;

pulsing the light beam at a known frequency greater than 0.5 kHz;

scanning the light beam around the eye in a trajectory to determine a position of the eye, the position being determined from a variation in the intensity of the reflected energy;

synchronizing the step of pulsing with the step of scanning;

overlapping a position of the light beam at maximum intensity with a previous position of the light beam at maximum intensity during the step of scanning;

blanking the visible light beam around a portion of the trajectory over the detected flap;

interpolating the measured intensity between measured values of the reflected energy;

positioning the trajectory to be substantially coincident with the limbus;

rotating the light beam around the eye at a reference frequency in a pattern comprising an annular trajectory so as to generate a varying corneal margin signal at the reference frequency;

comparing an amplitude of the varying signal with a reference to determine a magnitude of an eye displacement;

comparing a phase angle of the varying signal with the reference so as to determine an angle of the position of the eye; and displacing the trajectory so as to minimize the variation in intensity of the reflected energy, the location of the trajectory corresponding to the position of the eye, and a separation distance between an initial location of the trajectory and the displaced location of the trajectory being greater than a dimension across the measured region.

40. The method of claim 39, further comprising:

restricting a dimension across the measured region by selectively passing light rays from within the region to a light energy detector and excluding light rays from outside the region from the light energy detector; and deflecting the beam with a beam deflection module, the beam deflection module comprising an optical element selected from the group consisting of lenses, prisms and mirrors.

41. A method of treating an eye with a beam of a laser treatment energy, the eye having a limbus and the beam having a path, the method comprising:

directing a light energy at the eye;

measuring an intensity of the light energy reflected from a region of the eye, the region including a portion of the limbus;

automatically detecting an excised flap of tissue covering the limbus of the eye; and applying the treatment energy to a tissue structure on the eye.

42. The method of claim 41 further comprising:

projecting a beam of a visible light energy at the eye to form a visible light spot on an uncovered portion of the limbus;

scanning the measured region around the eye to determine a position of the eye, the position being determined from a variation in the intensity of the reflected energy;

rotating the measured region around the eye at a reference frequency in a pattern comprising an annular trajectory to generate a varying corneal margin signal at the reference frequency;

comparing an amplitude of the varying signal with a reference to determine a magnitude of an eye displacement;

comparing a phase angle of the varying signal with the reference so as to determine an angle of the position of the eye;

positioning the trajectory to be substantially coincident with the limbus;

displacing the trajectory so as to minimize the variation in intensity of the reflected energy, the location of the displaced trajectory corresponding to the position of the eye; and separating an initial location of the trajectory from a displaced location of the trajectory by a distance greater than a dimension across the measured region.

43. A method of laser sculpting a laser treatment area of an eye to a predetermined shape with a series of pulses from a beam of an ablative laser energy, the method comprising:

offsetting a path of the laser beam from a reference position between pulses of the laser beam;

displacing an axis of an eye tracker from an initial position to a current position, the initial and the current positions of the axes being related to an initial and a current position of the eye, the eye tracker axis being independently movable from the laser beam path; and ablating the eye with the beam of ablative energy so as to sculpt the eye to the predetermined shape.

44. The method of claim 43, further comprising;

inputting a laser treatment into a laser system controller;

calculating a laser treatment table, the laser treatment table comprising an offset position of the beam from the reference position;

loading the laser treatment table in a random access memory of a laser system controller;

aligning the eye with the laser treatment area;

determining the initial position of the eye, the initial position being the position of the eye being obtained during the step of aligning;

storing the initial position of the eye in the random access memory of the laser system controller;

determining the current position of the eye;

calculating a displacement of the eye from the initial position to the current position;

comparing the displacement of the eye to a tolerance;

pausing the laser treatment if the displacement of the eye is greater than the tolerance;

calculating a new offset position of the eye by adding the offset position of the beam in the table to the displacement of the eye;

moving an element of a laser beam deflection module according to the new offset position;

pulsing the laser beam;

repeating steps of determining the current position of the eye through pulsing the laser beam; and ending the laser treatment.

45. An eye tracker for measuring a position of an eye, the eye having a boundary, the tracker comprising:

a light source for making a light energy;

a light detector positioned to receive the light energy reflected from a region of the eye, the region including a portion of the boundary;

an optically non-transmitting material with an aperture formed in the material for restricting a dimension across the measured region by selectively passing the light energy from the region through the aperture to the detector, the material blocking light rays from outside the measured region;

an optical train for scanning the region around the eye in a trajectory;

a controller coupled to the light detector for measuring the reflected light energy to determine a relative position of the eye.

46. The eye tracker of claim 45, further comprising:

an imaging lens for imaging the region onto the aperture.

47. An eye tracker for measuring a position of an eye, the eye having a boundary, the tracker comprising:

a visible light source for making a light energy;

an imaging lens for projecting the light energy onto the eye as a visible light spot;

a light detector positioned to receive the light energy reflected from a region of the eye, the region including a portion of the boundary;

an optically non-transmitting material with an aperture formed in the material for restricting a dimension across the measured region by selectively passing the light energy from the region through the aperture to the detector, the material blocking light rays from outside the measured region;

an optical train for scanning the region around the eye in a trajectory;

a controller coupled to the light detector for measuring the reflected light energy to determine a relative position of the eye.

48. The eye tracker of claim 47, further comprising:

a light beam deflection module for scanning the light spot and the measured region around the eye in an annular trajectory;

a reflecting surface for aligning the projected light spot with the measured region so as to be confocal on the eye.

49. An eye tracker for measuring a position of an eye, the eye having a boundary, the tracker comprising:

a display screen comprising a light spot comprising a visible light energy;

an imaging lens for projecting the light energy onto the eye as a visible light spot;

a light detector positioned to receive the light energy reflected from a region of the eye, the region including a portion of the boundary; and a controller coupled to the light detector for measuring the reflected light energy to determine a relative position of the eye.

50. The eye tracker of claim 49, further comprising:

a tunable bandpass filter for filtering a corneal margin signal;

a peak hold detector for holding a signal peak;

a phase comparator coupled to a reference signal for determining a phase angle of the signal peak; and a divider for dividing the signal peak by a reference.

51. An eye tracker for measuring a position of an eye, the eye having a boundary, the tracker comprising:

a light source for making a light energy;

a light detector positioned to receive the light energy reflected from a region of the eye, the region including a portion of the boundary;

an optical train for scanning the region over the eye; and a controller coupled to the light detector for automatically detecting a tissue covering the boundary, and measuring the reflected light energy from an uncovered portion of the boundary to determine a relative position of the eye.

52. The eye tracker of claim 51, further comprising:

an imaging lens for projecting the light energy onto the eye as a visible light spot, the light energy comprising a visible light energy;

an optically non-transmitting material with an aperture formed in the material for restricting a dimension across the measured region by selectively passing the light energy from the region through the aperture to the detector, the material blocking light rays from outside the measured region;

a light beam deflection module for scanning the light spot and the measured region around the eye in an annular trajectory;

a reflecting surface for aligning the projected light spot with the measured region so as to be confocal on the eye;

a blanking circuit for blanking the projected visible light spot over the detected tissue covering the boundary, the boundary comprising a portion of the limbus;

an automatic flap detection circuit for detecting a flap of incised tissue;

an interpolation circuit for interpolating the measured light energy; and an offset circuit for displacing the annular trajectory to match the position of the eye.

53. The eye tracker of claim 51 wherein the light source comprises a display screen.

54. The eye tracker of claim 53, further comprising:

an imaging lens for projecting the light energy onto the eye as a visible light spot, the light energy comprising a visible light energy;

a blanking circuit for blanking the projected visible light spot over the detected tissue covering the boundary, the boundary comprising a portion of the limbus;

an interpolation circuit for interpolating the measured light energy; and an offset circuit for displacing the annular trajectory to match the position of the eye.

55. A laser surgery system integrated with an eye tracker, the system comprising:

a laser for generating a beam of an ablative laser energy;

a movable laser beam path that is variably offset from a reference position;

a movable eye tracker axis, the eye tracker axis being movable so as to match a position of the eye, the eye tracker axis further being independently movable relative to the laser beam path;

a laser system controller for offsetting the laser beam path according to a position of the eye tracker axis and value of a laser treatment table.

56. The laser surgery system of claim 55, further comprising:

a light source for making a visible light energy;

a light detector positioned to receive the light energy reflected from a region of the eye, the region including a portion of the boundary;

an optical train for scanning the region over the eye;

an eye tracker controller coupled to the light detector for automatically detecting a tissue covering the boundary, and measuring the reflected light energy from an uncovered portion of the boundary to determine a relative position of the eye;

an imaging lens for projecting the light energy onto the eye as a visible light spot, the light energy comprising a visible light energy;

a blanking circuit for blanking the projected visible light spot over the detected tissue covering the boundary, the boundary comprising a portion of the limbus;

an interpolation circuit for interpolating the measured light energy; and an offset circuit for displacing the annular trajectory to match the position of the eye.

57. An integrated eye tracker and laser surgery system for laser sculpting a cornea of an eye to a predetermined shape, the eye having a boundary, the system comprising:

a laser for generating a beam of an ablative laser energy;

a light source for making a visible light energy;

a light detector positioned to receive the light energy reflected from a region of the eye, the region including a portion of the boundary;

a laser beam deflection module for offsetting a path of the beam and an axis of the eye tracker;

an eye tracker controller coupled to the light detector for automatically detecting a tissue covering the boundary, and measuring the reflected light energy from an uncovered portion of the boundary to determine a relative position of the eye; and a laser system controller for offsetting the laser beam path according to a position of the eye tracker axis and a value of a laser treatment table.

58. The laser surgery system of claim 57, further comprising:

an imaging lens for projecting the light energy onto the eye as a visible light spot;

a blanking circuit for blanking the projected visible light spot over the detected tissue covering the boundary, the boundary comprising a portion of a limbus of the eye;

an interpolation circuit for interpolating the measured light energy; and an offset circuit for displacing the measured region to match the position of the eye.

\* \* \* \* \*